US012642824B2

(12) United States Patent
Pascual et al.

(10) Patent No.:  US 12,642,824 B2
(45) Date of Patent:        Jun. 2, 2026

(54) LACTOCOCCAL EXPRESSION OF IL-35 FOR TREATMENT OF DISEASE

(71) Applicant: Montana State University, Bozeman, MT (US)

(72) Inventors: David Pascual, Gainesville, FL (US); Massimo Maddaloni, Gainesville, FL (US)

(73) Assignee: Montana State University, Bozeman, MT (US)

( * ) Notice: Subject to any disclaimer, the term of this patent is extended or adjusted under 35 U.S.C. 154(b) by 1068 days.

(21) Appl. No.: 17/637,987

(22) PCT Filed: Aug. 28, 2020

(86) PCT No.: PCT/US2020/048467
§ 371 (c)(1),
(2) Date: Feb. 24, 2022

(87) PCT Pub. No.: WO2021/041855
PCT Pub. Date: Mar. 4, 2021

(65) Prior Publication Data
US 2022/0280580 A1      Sep. 8, 2022

Related U.S. Application Data

(60) Provisional application No. 62/893,074, filed on Aug. 28, 2019.

(51) Int. Cl.
*A61K 35/744*        (2015.01)
*A61K 35/20*         (2006.01)
(Continued)

(52) U.S. Cl.
CPC ............ *A61K 35/744* (2013.01); *A61K 35/20* (2013.01); *A61P 37/06* (2018.01); *C07K 14/54* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 9,452,205 B2 | 9/2016 | Pascual et al. |
| 2013/0164380 A1 | 6/2013 | Durum et al. |
| 2016/0243221 A1 | 8/2016 | Hoge et al. |

FOREIGN PATENT DOCUMENTS

| | | | |
|---|---|---|---|
| CN | 109628461 A | * | 4/2019 |
| WO | WO-2015168534 A1 | * | 11/2015 ............... C12N 9/20 |

OTHER PUBLICATIONS

Maddaloni, et. al., "Delivery of IL-35 by Lactococcus lactis Ameliorates Collagen-Induced Arthritis in Mice", Frontiers in Immunology, vol. 9, Article 2691, 2018, pp. 1-9.

(Continued)

*Primary Examiner* — Robert J Yamasaki
*Assistant Examiner* — Charles Zoltan Constantine
(74) *Attorney, Agent, or Firm* — Tanya M. Harding; Lee & Hayes, P.C.

(57) ABSTRACT

The present disclosure relates generally to therapeutic compositions comprising recombinant bacteria. Further, the disclosure elaborates upon methods of utilizing the herein described therapeutic compositions to treat autoimmune and inflammatory disease. The present teachings also relate to the disclosed recombinant bacteria and methods of producing the recombinant bacteria utilized in the compositions and methods. Further taught herein are dietary supplements and food additive compositions comprising the taught recombinant bacteria.

17 Claims, 11 Drawing Sheets

Specification includes a Sequence Listing.

(51) Int. Cl.
     *A61K 38/00*      (2006.01)
     *A61P 37/06*      (2006.01)
     *C07K 14/54*      (2006.01)

(56)                References Cited

OTHER PUBLICATIONS

Maddaloni, et. al., "Milk-Based Nutraceutical for Treating Autoimmune Arthritis via the Stimulation of IL-10- and TGF-B-producing CD39+ Regulatory T Cells", PLOS ONE, 2015, pp. 1-14.

GenBank Accession No. AAL01442, "bioactive single-chain murine interleukin 12 [synthetic construct]", Sep. 10, 2001; Accessed online Aug. 12, 2022 at ncbi.nlm.nih.gov/protein/AAL01442, 2 pages.

GenBank Accession No. ABK41923.1 "Epstein-Barr virus induced gene 3 [Homo sapiens]," Nov. 13, 2001; Accessed online Aug. 12, 2022 at ncbi.nlm.nih.gov/protein/ABK41923, 2 pages.

Aparicio-Siegmund, et al., "Recombinant p35 from bacteria can form Interleukin (IL-)12, but Not IL-35," PLoS One, vol. 9, No. 9, 2014, 13 pages.

Braat, et al., "A phase I trial with transgenic bacteria expressing interleukin-10 in Crohn's disease," Clin. Gastroenterol. Hepatol., vol. 4, No. 6, 2006, pp. 754-759.

Collison, et al., "IL-35-mediated induction of a novel regulatory T cell population," Nat. Immunol., vol. 11, No. 12, 2010, pp. 1093-1101.

Collison, et al., "The composition and signaling of the IL-35 receptor are unconventional," Nat. Immunol., vol. 13, No. 3, 2012, pp. 290-299.

GenBank Accession No. FJ5555208.1, "Shuttle vector pMSP3535H3, complete sequence," Apr. 23, 2001; Accessed online Aug. 12, 2022 at ncbi.nlm.nih.gov/nucleotide/FJ555208.1?report=genbank&log$=nucltop&blast_rank=1&RID=FDY3GM4R01R, 5 pages.

Huang, et al., "Interleukin-35 on B cell and T cell induction and regulation," J. Inflamm. (Lond). vol. 14, No. 16, 2017, 7 pages.

Kluger, et al., "Stat3 programs Th17-specific regulatory T cells to control GN," J. Am. Soc. Nephrol., vol. 25, No. 6, 2014, pp. 1291-1302.

Kochetkova, et al., "IL-35 stimulation of CD39+ regulatory T cells confers protection against collagen II-induced arthritis via the production of IL-10," J. Immunol, vol. 184, No. 12, 2010, pp. 7144-7153.

Magid-Bernstein, et al., "Human CD39 + T reg Cells Express Th17-Associated Surface Markers and Suppress IL-17 via a Stat3-Dependent Mechanism," J. Interferon. Cytokine Res., vol. 37, No. 4, 2017, pp. 153-164.

McLean, et al., "Interleukin-27 Is a Potential Rescue Therapy for Acute Severe Colitis Through Interleukin-10-Dependent, T-Cell-Independent Attenuation of Colonic Mucosal Innate Immune Responses," Inflamm. Bowel Dis., vol. 23, No. 11, 2017, pp. 1983-1995.

Niedbala, et al., "IL-35 is a novel cytokine with therapeutic effects against collagen-induced arthritis through the expansion of regulatory T cells and suppression of Th17 cells," Eur. J. Immunol., vol. 37, No. 11, 2007, pp. 3021-3029.

GenBank Accession No. NP_000873.2, "interleukin-12 subunit alpha isoform 1 precursor [Homo sapiens]," Jun. 12, 2022; Accessed online Aug. 12, 2022 at https://www.ncbi.nlm.nih.gov/protein/NP_000873.2, 3 pages.

GenBank Accession No. NP_056581.1 "interleukin-27 subunit beta precursor [Mus musculus]," Feb. 15, 2022; Accessed online Aug. 12, 2022 at https://www.ncbi.nlm.nih.gov/protein/NP_056581.1, 3 pages.

Richards, et al., "Dietary metabolites and the gut microbiota: an alternative approach to control inflammatory and autoimmune diseases," Clin. Transl. Immunology, vol. 5, No. 5, 2016, 8 pages.

Schorpion & Kolasinski, "Can Probiotic Supplements Improve Outcomes in Rheumatoid Arthritis?" Curr. Rheumatol. Rep., vol. 19, No. 73, 2017, 7 pages.

Shigemori & Shimosato, "Applications of Genetically Modified Immunobiotics with High Immunoregulatory Capacity for Treatment of Inflammatory Bowel Diseases," Front. Immunol., vol. 8, No. 22, 2017, 11 pages.

Singh, et al., "Interleukin-35 administration counteracts established murine type 1 diabetes—possible involvement of regulatory T cells," Sci. Rep., vol. 5, No. 12633, 2015, 19 pages.

Steidler, et al., "Biological containment of genetically modified Lactococcus lactis for intestinal delivery of human interleukin 10," Nat. Biotechnol., vol. 21, No. 7, 2003, pp. 785-789.

Tirotta, et al., "Epstein-Barr virus-induced gene 3 negatively regulates neuroinflammation and T cell activation following coronavirus-induced encephalomyelitis," J. Neuroimmunol, vol. 254, No. 1-2, 2013, pp. 110-116.

Wang, et al., "IL-35 recombinant protein reverses inflammatory bowel disease and psoriasis through regulation of inflammatory cytokines and immune cells," J. Cell. Mol. Med., vol. 22, No. 2, 2018, pp. 1014-1025.

Wang, et al., "Interleukin-35 induces regulatory B cells that suppress CNS autoimmune disease," Nat. Med., vol. 20, No. 6, 2014, pp. 633-641.

Yamashita, et al., "Lactobacillus helveticus SBT2171 Attenuates Experimental Autoimmune Encephalomyelitis in Mice," Front. Microbiol., vol. 8, No. 2596, 2018, 10 pages.

* cited by examiner

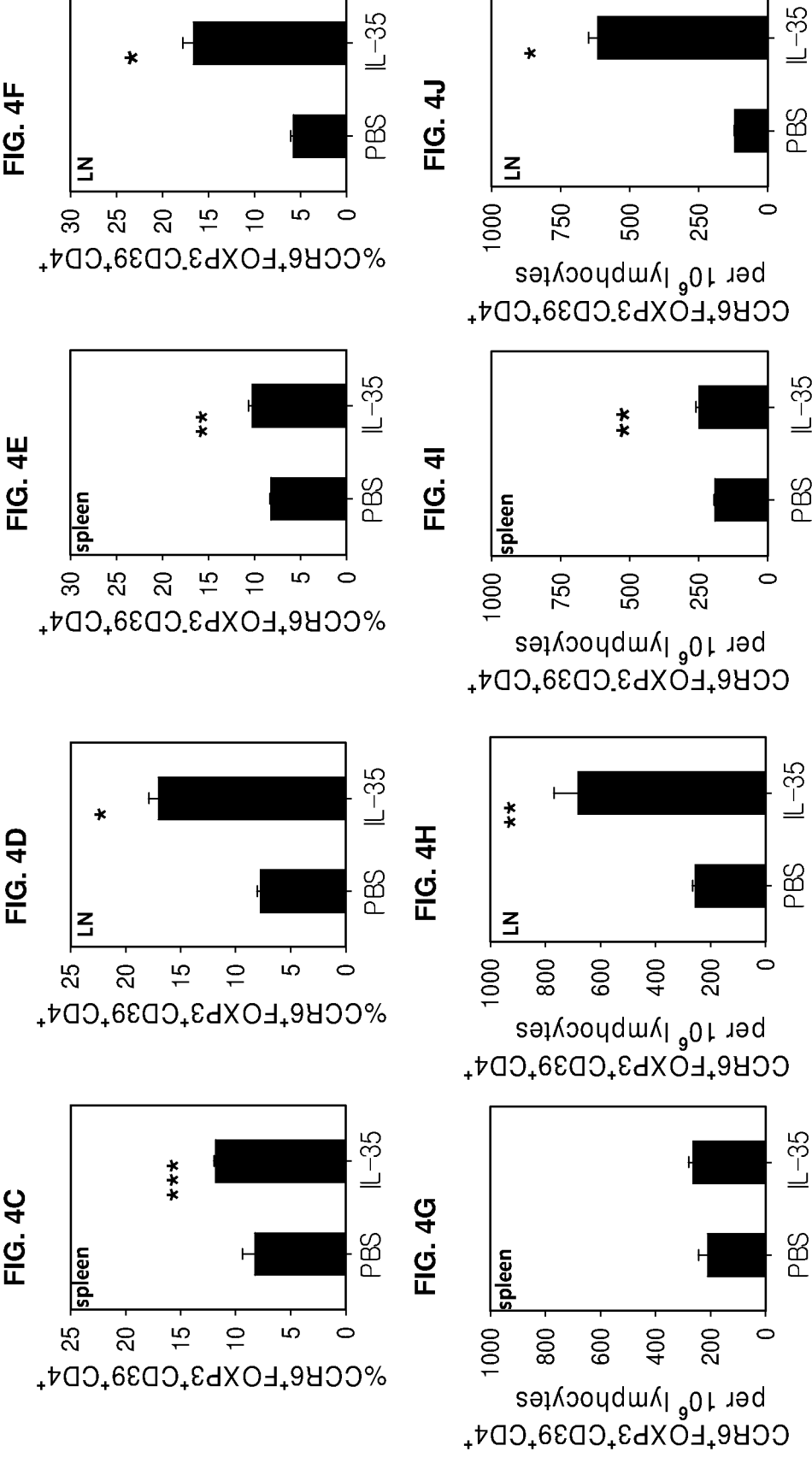

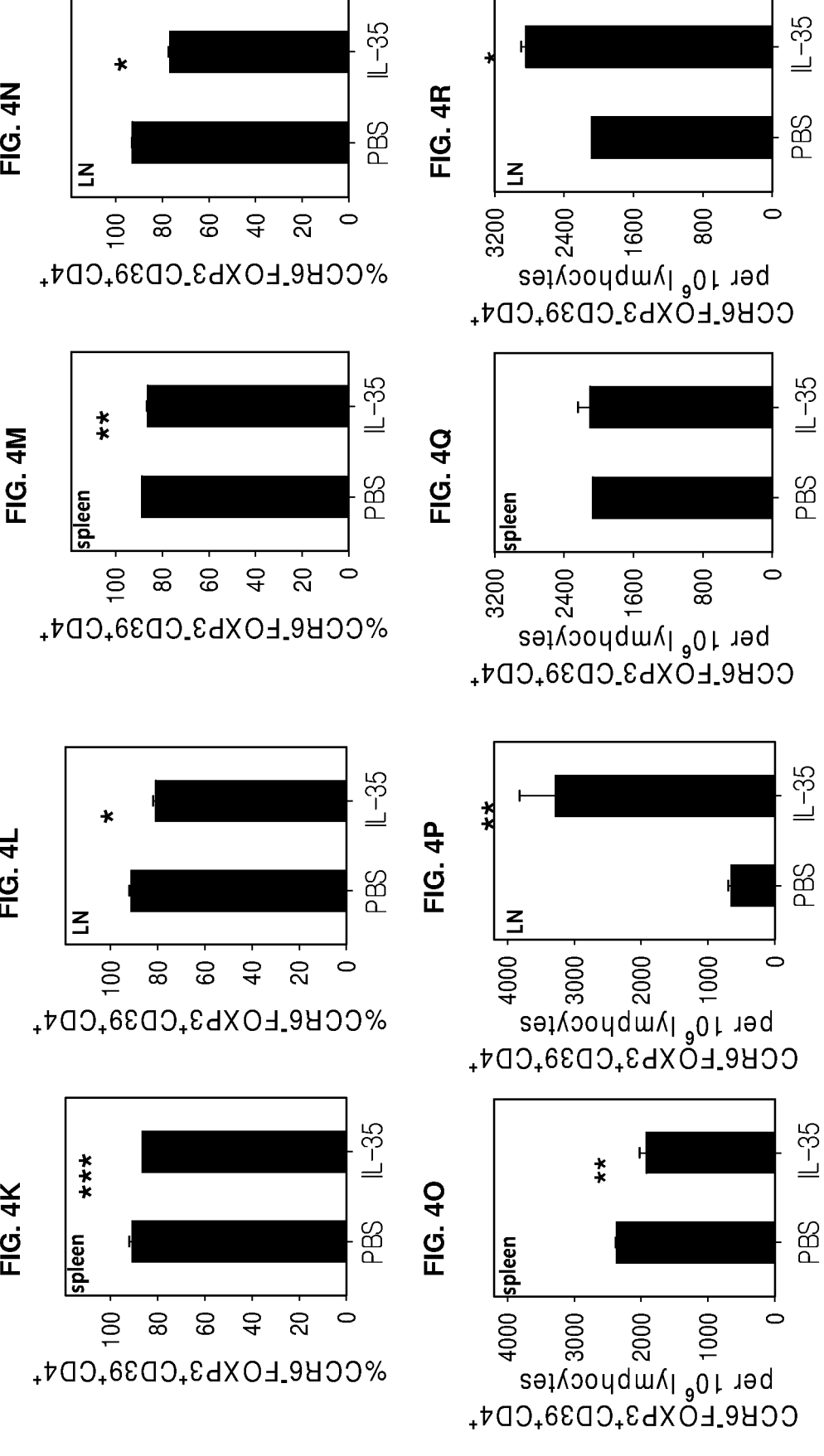

Marker
Empty vector
Unloaded well

No histag
pGnMM60
pGnMM60

+ histag
pGnMM63
pGnMM63 pGnMM63
Late induction

100 KDa
75 KDa
50 KDa
37 KDa

Usp45 SP

Flex linker GlyAlaGlyGly. Different from pBzMM150 (GPG)

pGnMM60 pGnMM121

Mouse EBI-3    Mouse p-35

Usp45 SP    Rigid linker

Backbone:
pMSP3535H3

Marker

Clone
1    2    3

L. Lactis IL1403
pMSP3535H3
pBzMM150

75 KDa
50 KDa
37 KDa pBzMM150 (Usp45 signal peptide-p35-flex linker-EBI3 IL-35)

LACTOCOCCAL EXPRESSION OF IL-35 FOR TREATMENT OF DISEASE

CROSS-REFERENCE TO RELATED APPLICATION

This is the 371 U.S. National Phase of PCT/US2020/048467, filed Aug. 28, 2020; which claims priority to and the benefit of the earlier filing date of U.S. Provisional Application No. 62/893,074, filed on Aug. 28, 2019, which is incorporated by reference herein in its entirety.

STATEMENT REGARDING FEDERALLY SPONSORED RESEARCH OR DEVELOPMENT

This invention was made with government support under contract AR-058010 awarded by the National Institutes of Health. The government has certain rights in the invention.

FIELD OF THE DISCLOSURE

The present disclosure relates generally to therapeutic compositions including recombinant bacteria, such as recombinant lactic acid bacteria, and methods of using the recombinant bacteria and therapeutic compositions containing them to treat autoimmune and inflammatory disease. Further taught herein are dietary supplements and food additive compositions including the herein described recombinant bacteria.

BACKGROUND OF THE DISCLOSURE

Autoimmune diseases are characterized by the body's immune responses being directed against its own tissues, causing prolonged inflammation and subsequent tissue destruction. For instance, autoimmune disorders can cause immune-responsive cells to attack the linings of the joints or trigger immune cells to attack the insulin-producing islet cells of the pancreas, leading to rheumatoid arthritis and insulin-dependent diabetes mellitus respectively.

In contrast, a healthy immune system recognizes, identifies, remembers, attacks, and destroys bacteria, viruses, fungi, parasites, cancer cells, or any health-damaging agents not normally present in the body. A defective immune system, on the other hand, wreaks havoc throughout the host by directing antibodies against its own tissues as well as cell-mediated immune responses.

Generally, a disease in which cytotoxic cells and antibodies are directed against self-antigens in the body's tissues is considered autoimmune in nature. Such diseases include celiac disease, Crohn's disease, pancreatitis, systemic lupus erythematosus, Sjogren's syndrome, Hashimoto's thyroiditis, and other endocrinopathies. Allergies and multiple sclerosis are also the result of disordered immune functioning.

Rheumatoid arthritis (RA) is a chronic, inflammatory, systemic autoimmune disease that affects about 0.24% of the worldwide population, and 1% of the general population in Western countries. RA is two to three times more common in women than in men (Hunter et al., *Rheumatol Int.* 37(9):1551-1557, 2017; Cross et al., *Ann. Rheum. Dis.* 1316-1322, 2014; Barbour et al., *MMWR Morb. Mortal. Wkly. Rep.* 66: 246-253, 2017; Carmona et al., *Best Pract. Res. Clin. Rheumatol.* 24: 733-745. 2010; Scott et al., *Lancet* 376: 1094-108, 2012). RA manifests as a chronic synovitis and progressive destruction of the joints, leukocyte infiltrates, and cartilage destruction and bone erosion. Approximately half of the afflicted patients become disabled over the progression of this disease (de Lange-Brokaar et al., *Osteoarthritis Cartilage* 12: 1484-499, 2012). RA is mediated predominantly by CD4+ T cells overexpressing proinflammatory cytokines, particularly in the joints (Jung et al., *J Immunol Res.* 2014:263625. doi: 10.1155/2014/263625).

In order to test the efficacy of potential RA therapeutics and understand mechanisms of disease, the collagen-induced arthritis (CIA) model is often used (Hegen et al., *Ann Rheum Dis.* 67(11):1505-15, 2008). CIA is typically induced by immunizing rodents with bovine or chick type II collagen together with an adjuvant. This combination leads to immune attack of the host's native collagen involving components of both the innate and adaptive immune systems. Emphasis on regulating proinflammatory cytokines, particularly TNF-α, is key to minimizing disease since TNF-α can be detected in joints of RA patients (Saxne et al., *Arithitis Rheum.* 31:1041-1045, 2018; Firestein et al., *J. Immunol.* 144:3347-3353, 1990). Mouse CIA shares several clinical, histopathological and immunological features with human RA. Clinical features include erythema, edema, synovitis, pannus formation, and CD4+ T cell-mediated inflammation with extensive cartilage and bone damage, resulting in joint deformities (Brand et al., *Methods Mol. Med.* 102: 295-312, 2004; Kannan et al., *Pathophysiology* 12: 167-181, 2005; Hu et al., *Clin. Rheumatol.* 32: 161-165, 2013). These similarities are commonly exploited to use CIA as a model for RA and as a tool to investigate novel approaches to prevent and treat RA. Current treatments focus on neutralizing TNF-α action via anti-TNF-α mAbs and TNF-α receptor antagonists (Kourbeti et al., *Clin Infect Dis.* 58(12): 1649-57, 2014; Rosenblum & Amita, *Autoimmun. Rev.* 10: 563-568, 2011); however, such interventions have been problematic, making patients more susceptible to opportunistic infections (Kourbeti et al., *Clin Infect Dis.* 58(12): 1649-57, 2014; Rosenblum & Amita, *Autoimmun. Rev.* 10: 563-568, 20111 Keyser *Curr. Rheumatol. Rev.* 7: 77-87, 2011). Hence, alternatives that can restore tolerance need to be sought.

In view of reducing autoimmunity, the use of probiotics can restore immune homeostasis to reduce autoimmunity (Yamashita et al., *Front Microbiol.* 8:2596, 2018; Schorpion & Kolasinski, *Curr Rheumatol Rep.* 19(11):73, 2017; Richards et al., *Clin Transl Immunology* 5(5):e82, 2016). Historically, lactic acid bacteria (LAB) represented the core of probiotic-based interventions, although more recently nonpathogenic *E. coli* (Kandasamy et al., *Front Immunol.* 8:334, 2017; Sonnenborn, *FEMS Microbiol Lett.* 363(19), 2016; et al., *Appl Microbiol Biotechnol.* 100(20):8693-9, 2016), attenuated *Salmonella* (Galen & Curtiss, *Vaccine* 32(35): 4376-85, 2014; Clark-Curtiss & Curtiss, *J Immunol.* 200(1): 39-48, 2018), *Bifidobacterium* spp. (Kirmiz et al., *Annu Rev Food Sci Technol.* 9:429-450, 2018), and some yeasts like *Saccharomyces boulardii* (More & Vandenplas, *Clin Med Insights Gastroenterol.* 11:1179552217752679, 2018) also proved to be valuable tools as novel therapeutic and prophylactic interventions. Traditional molecular genetics, coupled with synthetic biology, provides an ample selection of promoters and terminators resulting in dynamic expression levels. Protein synthesis can be induced in vitro under nisin controlled expression (NICE), or use a promoter that is silent during in vitro culture, and only active in vivo subsequent infection of the host (Mays & Nair, *Curr Opin Biotechnol.* 53:224-231, 2018; Kong et al., *Nucleic Acids Res.* 45(2):1005-1014, 2017; Desmond et al., *Appl Environ Microbiol.* 70(10):5929-36, 2004). LABs are considered ideal vectors for oral or mucosal delivery since they are inherently nonpathogenic, and they can survive the harsh conditions of the gastric environment. LABs are amenable to recombinant expression of passenger antigens (Ags) to stimulate immunity against a number of pathogens (Mansour & Abdelaziz, *Microbiol Immunol.* 60(8):527-32, 2016; O'Flaherty & Klaenhammer, *Appl Environ Microbiol.* 82(20):6091-6101, 2016; Li et al., *Oncol Lett.* 7(2):576-582, 201), to curb the effects of inflammatory bowel disease (Carvalho et al., *Front Microbiol.* 8:800, 2017; Del Carmen et al., *Appl Environ Microbiol.* 80(3):869-77, 2014), to control the proliferation of cancer cells (Zhang et al., *Microb Cell Fact.* 15(1):102, 2016), and to use for enzyme replacement therapy (Durrer et al., *PLoS One.* 12(5):e0176286, 2017) among other applications (Mays & Nair, *Curr Opin Biotechnol.* 53:224-231, 2018; Shigemori & Shimosato, *Front Immunol.* 8:22, 2017; Cano-Garrido et al., *Microb Cell Fact.* 14:137, 2015). Currently, the only microbiota-based therapy that is FDA-approved and commercially available is fecal microbiota transplant (FMT) to treat *Clostridium difficile* infections. However, close to 200 microbiome-based therapeutics and diagnostics are currently in development (*Microbiome Therapeutics and Diagnostics Market,* 2017-2030. Available online at researchandmarkets.com/research/ls8jkv/microbiome).

The delivery of oral therapeutics represents a significant advantage of adapting LABs. In this context, recombinant *Lactococcus lactis* (LL) has been developed for oral delivery to treat autoimmune disease (Maddaloni et al., *PLoS One.* 10(1):e0117825, 2015; U.S. Pat. No. 9,452,205). In a similar fashion, the studies described here focus on the expression of the immunosuppressive cytokine, IL-35. Oral administration of probiotic-based therapeutics is considered ideal because the gastrointestinal (GI) tract is home to T cells that can be stimulated to become Tregs and to seed other mucosal and systemic immune compartments. Another advantage of using genetically modified (GM) probiotics is that these have been shown to be both effective and safe (Shigemori & Shimosato, *Front Immunol.* 8:22, 2017; McLean et al., *Inflamm Bowel Dis.* 23(11):1983-1995, 2017; Braat et al., *Clin Gastroenterol Hepatol.* 4(6):754-9, 2006; Steidler et al., *Nat Biotechnol.* 21(7):785-9, 2003). Previous work has shown that an engineered LL derived from an industrial dairy strain can ferment commercial milk to a yogurt-like product, and when applied for treatment of CIA, can maintain the same therapeutic properties as when grown on a synthetic medium (Maddaloni et al., *PLoS One.* 10(1): e0117825, 2015). See also U.S. Pat. No. 9,452,205.

IL-35 belongs to the IL-12 cytokine family (reviewed in Huang et al., *J Inflamm* (Lond). 14:16, 2017). This heterodimeric cytokine is composed of IL-12p35 and IL-27EBI3 and, in contrast to most members of the IL-12 family, has potent anti-inflammatory attributes. This property is mediated via IL-35 binding both IL-12Rβ2 chain and gp130, which results in specific triggering of STAT1 and STAT4 on T cells (Collison et al., *Nat Immunol.* 13(3):290-9, 2012) and IL-12Rβ2 and IL-27Rβ on B cells (Wang et al., *Nat Med.* 20(6):633-41, 2014). IL-35 is immunosuppressive for a number of autoimmune disease models including CIA (Niedbala et al., *Eur J Immunol.* 37(11):3021-9, 2007; Kochetkova et al., *J Immunol.* 184(12):7144-53, 2010), experimental autoimmune encephalomyelitis (Collison et al., *Nat Immunol.* 11(12):1093-101, 2010; Tirotta et al., *J Neuroimmunol.* 254(1-2):110-6, 2013), uveitis (Wang et al., *Nat Med.* 20(6):633-41, 2014), type 1 diabetes (Singh et al., *Sci Rep.* 5:12633, 2015), inflammatory bowel disease (IBD0, and psoriasis (Wang et al., *J Cell Mol Med.* 22(2): 1014-1025, 2018).

CCR6 was previously shown to be expressed by Tregs (Kleinewietfeld et al., *Blood* 105(7):2877-86, 2005), particularly those expressing RoRyt (Rivino et al., *J Exp Med.* 207(3):565-77, 2010; Li et al., *Int J Clin Exp Med.* 8(9): 15043-53. 2015). These Tregs have been shown involved in suppressing autoimmune diseases (Smelt et al., *PLoS One* 7(10):e47244, 2012; Huibregtse et al., *Gastroenterology* 133(2):517-28, 2007; Borsellino et al., *Blood* 110: 1225-1232, 2007). CCR6[+] Tregs have been found more commonly associated with human Tregs (Li et al., *Int J Clin Exp Med.* 8(9):15043-53. 2015; Godefroy et al., *Gastroenterology* pii: S0016-5085(18)34720-6, 2018), but CCR6 has also been found to be induced in mice subjected to CIA (Li et al., *Int J Clin Exp Med.* 8(9):15043-53, 2015).

Therapeutic agents capable of preventing and/or reversing chronic inflammation is of particular interest to the medical community. Thus, the development of such a therapeutic is urgently needed in the art.

Furthermore, there is a need in the art for dietary supplements and food additives including elements that are beneficial to a subject's immune response.

SUMMARY OF THE DISCLOSURE

Described herein is the surprising discovery that mammalian IL-35 can be expressed in Gram-positive, Lactococcal bacteria. These live bacteria provide an effective vector for delivery of functional IL-35, for instance for treatment of diseases such as autoimmune diseases and disorders.

The disclosure therefore presents therapeutic compositions including recombinant Gram-positive bacteria expressing mammalian IL-35 that are beneficial for treating an autoimmune disease or disorder.

Furthermore, the present therapeutic compositions including the recombinant Gram-positive bacteria expressing mammalian IL-35 are beneficial for treating an inflammatory disease or disorder.

Products produced by the recombinant bacteria taught herein provide beneficial properties for the treatment of autoimmune and inflammatory diseases. That is, the protein sequences expressed by the described recombinant bacteria are demonstrated to be beneficial for the prevention and/or treatment of autoimmune and inflammatory diseases, and the amelioration of symptoms linked to such disease.

In particular embodiments, the recombinant Gram-positive bacteria expressing the mammalian IL-35 belong to the lactic acid bacterial clade. Some embodiments utilize members of the Order Lactobacillales as the recombinant bacterial host for the engineered, single-chain mammalian IL-35 gene. In some embodiments, the order of the subunits is IL-12α (p35) then IL-27β (EBI3); in others, the order is reversed—IL-27β (EBI3) then IL-12α (p35). Optionally, there is a rigid or a flexible linker between the two subunits.

Yet other embodiments employ members of the Family Streptococcaceae as the recombinant bacterial host for the engineered, single-chain mammalian IL-35 gene. Yet still other embodiments use bacteria from the Genus *Lactococcus* to host the engineered, single-chain mammalian IL-35 gene. One particular embodiment utilizes the bacterial species *Lactococcus lactis* to express and optionally secrete the engineered, single-chain mammalian IL-35 gene.

The current disclosure provides a composition, including: a recombinant lactic acid bacterial cell (for instance, from the genus *Lactococcus*) including a nucleotide sequence encoding an engineered, single-chain mammalian IL-35. By way of example, the composition may be formulated for treatment of an autoimmune or inflammatory disease.

In example compositions, the recombinant lactic acid bacterial cell expresses at least one heterologous IL-35 nucleic acid encoding the engineered, single-chain mammalian polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 11, 5, or 6 that has at least 85%, at least 90%, at least 95%, or at least 98% sequence identity to that sequence.

In example compositions, the recombination lactic acid bacterial cell expresses an engineered, single-chain mammalian IL-35 protein including the amino acid sequence shown in SEQ ID NO: 2 (murine), SEQ ID NO: 11 (murine), SEQ ID NO: 5 (canine), or SEQ ID NO: 7 (human) from an engineered, single-chain mammalian IL-35 nucleic acid.

The engineered, single-chain mammalian IL-35 protein in any of the provided composition examples may be expressed from a transgene including the nucleotide sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence. Optionally, in any of the composition embodiments, the nucleotide sequence encoding the engineered, single-chain mammalian IL-35 is integrated into the genome of the recombinant lactic acid bacterial cell.

The compositions provided herein may be used to induce an anti-inflammatory response in a subject treated with the composition.

Examples of the various composition embodiments are a milk-based nutraceutical, for instance a fermented milk product. By way of example, the fermented milk product may include a yogurt, a buttermilk, a kefir, a cheese, a crème fraiche, or a cultured sour cream.

Also provided in another embodiment is use of any of the provided compositions for treating an inflammatory disease or condition, such as one or more of an allergy, asthma, autoimmune arthritis, celiac disease, Crohn's disease, diabetes, multiple sclerosis, systemic lupus erythematosus, Sjogren's syndrome, Hashimoto's thyroiditis, and/or another endocrinopathy.

Another embodiment is use of any one of the composition embodiments for stimulating IL-10 and TGF-β-producing CD39+ regulatory T cells.

Yet another embodiment is use of any one of the composition embodiments for stimulating one or more regulatory cell subsets including Foxp3 (FOXP3)$^+$ and Foxp3 (FOXP3)$^-$ T cells, CD25$^+$ and CD25$^-$ T cells, regulatory B cells, and regulatory innate cells involved in producing a tolerogenic condition.

Provided in another embodiment is a recombinant lactic acid bacterial cell (such as a cell from the genus *Lactococcus*), which cell includes: a nucleotide sequence encoding an engineered, single-chain mammalian IL-35. IN examples of this embodiment, the cell expresses at least one heterologous IL-35 nucleic acid encoding the engineered, single-chain mammalian polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 5, or 6 that has at least 85%, at least 90%, at least 95%, or at least 98% sequence identity to that sequence. In alternative and overlapping examples, the recombinant lactic acid bacterial cell expresses SEQ ID NO: 2 (murine), SEQ ID NO: 11 (murine), SEQ ID NO: 5 (canine), or SEQ ID NO: 7 (human) from an engineered, single-chain mammalian IL-35 nucleic acid.

In yet more examples of the recombinant lactic acid bacterial cell embodiments, the nucleotide sequence encoding the engineered, single-chain mammalian IL-35 includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence. Optionally, in any of the recombinant lactic acid bacterial cell embodiments, the nucleotide sequence encoding the engineered, single-chain mammalian IL-35 may be integrated into the genome of the recombinant lactic acid bacterial cell.

Another embodiment is a milk-based nutraceutical composition including: a recombinant lactic acid bacterial cell including a nucleotide sequence encoding an engineered, single-chain mammalian IL-35. In examples of this embodiment, the recombinant lactic acid bacterial cell expresses at least one heterologous nucleic acid encoding the engineered, single-chain mammalian IL-35 polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 5, or 6 that has at least 85%, at least 90%, at least 95%, or at least 98% sequence identity to that sequence.

Also provided are milk-based nutraceutical compositions, wherein the engineered, single-chain mammalian IL-35 includes the amino acid sequence of SEQ ID NO: 2 (murine), SEQ ID NO: 11 (murine), SEQ ID NO: 5 (canine), or SEQ ID NO: 7 (human). Optionally, in provided examples of the milk-based nutraceutical composition embodiments, the nucleotide sequence includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence. For instance, the nucleotide sequence may include the sequence of SEQ ID NO: 1 (murine), SEQ ID NO: 4 (canine), or SEQ ID NO: 6 (human).

Yet another embodiment is use of any of the provided milk-based nutraceutical compositions for treating an inflammatory disease or condition. By way of example, the inflammatory disease or condition may include one or more of an allergy, asthma, autoimmune arthritis, celiac disease, Crohn's disease, diabetes, multiple sclerosis, systemic lupus erythematosus, Sjogren's syndrome, Hashimoto's thyroiditis, and/or another endocrinopathy.

Also provided is use any of the provided milk-based nutraceutical compositions for stimulating IL-10 and TGF-β-producing CD39+ regulatory T cells.

Another provided use is use of any of the provided milk-based nutraceutical compositions for stimulating one or more regulatory cell subsets including Foxp3 (FOXP3)$^+$ and Foxp3 (FOXP3)$^-$ T cells, CD25$^+$ and CD25$^-$ T cells, regulatory B cells, and regulatory innate cells involved in producing a tolerogenic condition.

Provided herein in another embodiment is a method for treating or preventing an autoimmune or inflammatory disease in a subject, the method including: administering to the subject any one of the composition embodiments provided herein, or a composition including any one of the recombinant lactic acid bacterial cells provided herein. In examples of such methods of treating or preventing, the level of IL-10 in the subject is increased upon the administering, as compared to the level of the IL-10 present in the subject before the administering; and/or the level of TGF-β in the subject is increased upon the administering, as compared to the level of the TGF-β present in the subject before the administering; and/or the level of at least one of IFN-γ or IL-17 is decreased upon the administering, as compared to the level of at least one of IFN-γ or IL-17 present in the subject before the administering; and/or the level of TNF-α is decreased upon the administering, as compared to the level of TNF-α present in the subject before the administering.

Yet another embodiment is a method for producing a composition for the treatment of an autoimmune or inflammatory disease, including: introducing a nucleotide sequence encoding an engineered, single-chain mammalian IL-35 into a recipient lactic acid bacterial cell. In examples of this method embodiment, the engineered, single-chain mammalian IL-35 expresses at least one engineered, single-chain mammalian IL-35 including the amino acid sequence of SEQ ID NO: 2 (murine), SEQ ID NO: 11 (murine), SEQ ID NO: 5 (canine), SEQ ID NO: 7 (human) or a functionally equivalent variant of one of SEQ ID NO: 2, 11, 5, or 6 that has at least 85%, at least 90%, at least 95%, or at least 98% sequence identity to that sequence. In alternative and overlapping examples, the nucleotide sequence includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence. For instance, in some specific examples the nucleotide sequence includes the sequence of SEQ ID NO: 1 (murine), SEQ ID NO: 10 (murine), SEQ ID NO: 4 (canine), or SEQ ID NO: 6 (human).

Also provided are method of treating or preventing embodiments, which further include: culturing the lactic acid bacterial cell under conditions which allow for expression of the engineered, single-chain mammalian IL-35.

In examples of any of the method embodiments, wherein introducing the nucleotide sequence encoding the engineered, single-chain mammalian IL-35 includes integrating the encoding sequence into the genome of the recipient lactic acid bacterial cell.

Also taught herein are methods for producing a composition for the treatment of an autoimmune or inflammatory disease, including: introducing a nucleotide sequence encoding single-chain mammalian IL-35 into a recipient Gram-positive bacterial cell, e.g. a lactic acid bacterial cell, and culturing the recipient bacterial cell under conditions which allow for expression of the mammalian IL-35 protein.

The methods may further include packaging the recombinant bacterial cells with any pharmaceutically acceptable carrier, buffer, excipient, adjuvant, or mixture thereof.

The methods may further include packaging the recombinant bacterial cells with any foodstuff, such as a: beverage, dairy product, yogurt, fermented food, or the like.

The methods may further include packaging the recombinant bacterial cells with a food supplement, such as a: powdered composition, encapsulated composition, or any liquid formulation.

The recombinant bacterial cells taught herein may be live upon administration or may not. Further, the therapeutic compositions disclosed herein may include mixtures of both live and non-living recombinant bacterial cells.

In any of the provided embodiments, the engineered, single-chain mammalian polypeptide may include an EBI3/IL-27β subunit; a p35/IL-12α subunit; and a linker therebetween. For instance, the order of the components in some instances EBI3/IL-27β subunit-linker-p35/IL-12α subunit; in some instances, it is p35/IL-12α subunit-linker-EBI3/IL-27β subunit. In various exemplary engineered, single-chain mammalian polypeptides, the EBI3/IL-27β subunit is from human IL-35, from murine IL-35, or from canine IL-35; and/or the p35/IL-12α subunit is from human IL-35, from murine IL-35, or from canine IL-35; and/or the linker is a rigid peptide linker or a flexible peptide linker.

BRIEF DESCRIPTION OF THE DRAWINGS

(FIG. 1A) Schematic map of the synthetic DNA used to construct pBzMM150 for murine IL-35 expression of IL-35 in *L. lactis*. The synthetic insert encodes in order: the usp45 secretion peptide genetically fused in-frame to the p35 subunit, a short flexible linker, fused to the EBI3. The synthetic DNA also features an optimal Shine-Dalgarno (SD) sequence at the optimal distance from the ATG initiation codon, in addition to the SD sequence present in the vector. The nisin-inducible promoter and a transcription terminator are borne on the expression vector pMSP3535H3. (FIGS. 1B, 1C) CIA was induced in groups of C57BL/6 males with chick CII emulsified in complete Freund's adjuvant. Two regimens were tested: orally treated with $5 \times 10^8$ CFUs of LL vector or LL-IL35 or sterile PBS on (FIG. 1B) 14, 21, and 28 days or (FIG. 1C) 18- and 25-days post-induction. Average clinical score per treatment group (left panels) represents severity of the disease, and incidence of arthritis depicts percent mice with affected joints in each treatment group (right panels). The sum of 10 mice/group is shown: (FIG. 1B) *p<0.001 versus PBS-dosed or LL vector-treated mice, and (FIG. 1C) p<0.02, *p<0.05 versus PBS-dosed mice and ++p<0.02 versus LL vector-treated mice.

(FIG. 2A) Cell suspensions were analyzed by flow cytometry for Ly-6G+ CD11 b+ neutrophils, and (FIG. 2B) quantified per $10^6$ cells. The depicted plots are representative of 5 mice/group; *p<0.001 versus PBS-dosed mice; ##p<0.005 versus LL vector-treated mice. Scale in FIG. 2A is log, 0 to $10^5$ on both axes.

FIG. 6A is an image of a Western blot of canine IL-35 expressed without (pGnMM60) or with a carboxy Histag (pGnMM63). FIG. 6B is a linear map showing the sequential order of expressing p35 and EBI3 subunits.

FIG. 7A is a linear map showing the sequential order of expressing the EBI3 and p35 subunits in this exemplar. FIG. 7B shows Western blot detection of the original murine IL-35 construct (pBzMM150; arranged as in SEQ ID NO: 2); FIG. 7C shows Western blot detection of the murine IL-35 (pGnMM121; arranged as in SEQ ID NO: 10). ind.: "induction".

REFERENCE TO SEQUENCE LISTING

Figures 1A, 1B, 1C:
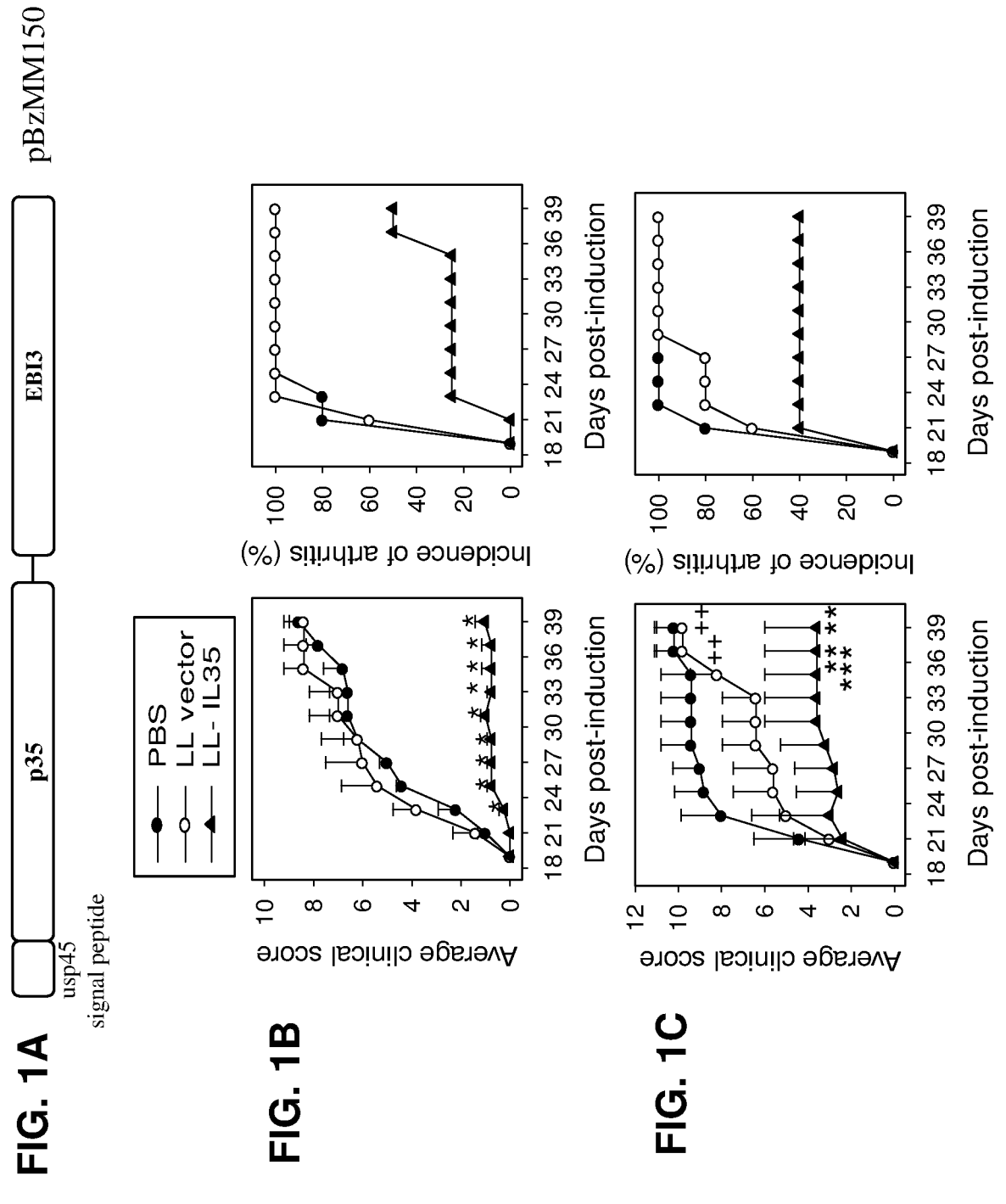
FIGS. 1A-1C. IL-35 inhibits CIA progression following treatment with LL-IL35.

The nucleic acid and amino acid sequences described herein and provided in the accompanying Sequence Listing are shown using standard letter abbreviations, as defined in 37 C.F.R. § 1.822. Only one strand of each nucleic acid sequence is shown, but the complementary strand is understood as included in embodiments where it would be appropriate. A computer readable text file, entitled "2ND7462.txt (Sequence Listing.txt)" created on Feb. 22, 2022, with a file size of 28 KB, contains the sequence listing for this application and is hereby incorporated by reference in its entirety.

SEQ ID NO: 1 is the nucleic acid sequence encoding an exemplary engineered, single-chain murine IL-35, the sequence of which has been optimized for expression in lactic acid bacteria. The codon usage was hand-optimized for *Lactococcus* but it has been designed to fit most Lactic acid bacteria except, perhaps, *Lactobacillus delbruekii* ssp. *bulgaricus* which has a peculiar codon usage. Within SEQ ID NO: 1:

| Positions | |
|---|---|
| 1-16 | cloning site (1-6: Age1; 7-12: Smal; 11-16: Kpnl) |
| 17-22 | Shine-Dalgarno sequence |
| 23-30 | 8 bp spacer |
| 31-33 | Start codon |

-continued

| Positions | |
|---|---|
| 31-120 | encodes usp45 signal peptide, including its physiological downstream sequence, AspThrAsn (DTN) (corresponding to positions 111-120), to improve the chance of correct processing. |
| 121-126 | a Nhel restriction site upstream of p35; this site facilitates mending intervention(s) that may have been needed. |
| 127-708 | encode the IL-12α portion of murine IL-35. |
| 709-717 | encode a flexible linker (GPG). |
| 718-1371 | encode the IL-27β portion of murine IL-35. |
| 1368-1371 | stop codon. |
| 1-6 and 1372-1377 | Agel restriction ends used for cloning. |

SEQ ID NO: 2 is the amino acid sequence of the single-chain murine IL-35 encoded by SEQ ID NO: 1. Within SEQ ID NO: 2:

| Positions | |
|---|---|
| 1-30 | usp45 signal peptide, including its physiological downstream sequence AspThrAsn (DTN) (corresponding to positions 28-30). |
| 31-32 | Ala-Ser resulting from inclusion of a Nhel restriction site upstream of p35. This site facilitates eventual mending intervention(s) that may have been needed. |
| 33-226 | the IL-12α portion of the engineered, single-chain murine IL-35. |
| 227-229 | a flexible linker (GPG). |
| 230-446 | the IL-27β portion of the engineered, single-chain murine IL-35. |

SEQ ID NO: 3 is the nucleic acid sequence of a nisin-inducible promoter, provided in intuitive 5'-3' orientation; it is provided in GenBank FJ5555208 in 3'-5' orientation. The full sequence of expression vector pMSP3535H3 is available at NCBI GenBank locus FJ555208.

SEQ ID NO: 4 is the nucleic acid sequence encoding an exemplary engineered, single-chain canine IL-35, the sequence of which has been optimized for expression in lactic acid bacteria (pGnMM54). Within SEQ ID NO: 4:

| Positions | |
|---|---|
| 1-6 | cloning site |
| 7-10 | stuffer sequence |
| 11-16 | Shine-Dalgarno sequence |
| 17-24 | 8 bp spacer |
| 25-27 | Start codon |
| 25-114 | encodes usp45 signal peptide, including its physiological downstream sequence, AspThrAsn (DTN) (corresponding to positions 106-114), to improve the chance of correct processing. |
| 115-120 | a Nhel restriction site upstream of p35; this site facilitates mending intervention(s) that may have been needed. |
| 121-711 | encode the IL-12α portion of canine IL-35. |
| 712-723 | encode a flexible linker (GAGG). |
| 724-1332 | encode the IL-27β portion of canine IL-35. |
| 1330-1332 | stop codon. |
| 1-6 | Agel restriction site; Agel restriction ends used for cloning. |
| 1339-1344 | Smal restriction site. |

SEQ ID NO: 5 is the amino acid sequence of the single-chain canine IL-35 encoded by SEQ ID NO: 4. Within SEQ ID NO: 5:

| Positions | |
|---|---|
| 1-30 | usp45 signal peptide, including its physiological downstream sequence AspThrAsn (DTN) (corresponding to positions 28-30). |
| 31-32 | Ala-Ser resulting from inclusion of a NheI restriction site upstream of p35. This site facilitates eventual mending intervention(s) that may have been needed. |
| 33-229 | the IL-12α portion of the engineered, single-chain canine IL-35. |
| 230-233 | a flexible linker (GAGG). |
| 234-435 | the IL-27β portion of the engineered, single-chain canine IL-35. |

SEQ ID NO: 6 is a nucleic acid sequence encoding an exemplary engineered, single-chain human IL-35, the sequence of which has been optimized for expression in lactic acid bacteria (pGnMM107). Within SEQ ID NO: 6:

| Positions | |
|---|---|
| 1-12 | cloning site (1-6: Age1; 7-12: Smal) |
| 13-16 | stuffer |
| 17-22 | Shine-Dalgarno sequence |
| 23-30 | 8 bp spacer |
| 31-33 | Start codon |
| 31-120 | encodes usp45 signal peptide, including its physiological downstream sequence, AspThrAsn (DTN) (corresponding to positions 111-120 in the encoded protein), to improve the chance of correct processing. |
| 121-126 | a NheI restriction site upstream of p35; this site facilitates mending intervention(s) that may have been needed. |
| 127-720 | encode the IL-12α portion of human IL-35. |
| 721-765 | encode a flexible linker ((GGGGS)₃). |
| 766-1395 | encode the IL-27β portion of human IL-35. |
| 1393-1395 | stop codon. |
| 1-6 and 1402-1407 | AgeI restriction ends used for cloning. |

SEQ ID NO: 7 is the amino acid sequence of the single-chain human IL-35 encoded by SEQ ID NO: 6. Within SEQ ID NO: 7:

| Positions | |
|---|---|
| 1-30 | usp45 signal peptide, including its physiological downstream sequence AspThrAsn (DTN) (corresponding to positions 28-30). |
| 31-32 | Ala-Ser resulting from inclusion of a NheI restriction site upstream of p35. This site facilitates eventual mending intervention(s) that may have been needed. |
| 33-230 | the IL-12α portion of the engineered, single-chain canine IL-35. |
| 230-245 | a flexible linker ((GGGGS)₃). |
| 246-454 | the IL-27β portion of the engineered, single-chain canine IL-35. |

SEQ ID NO: 8 is the amino acid sequence of a synthetic peptide linker.

SEQ ID NO: 9 is the amino acid sequence of a single repeat of a flexible synthetic peptide linker (GGGGS).

SEQ ID NO: 10 is the nucleic acid sequence encoding an exemplary engineered, single-chain murine IL-35, the sequence of which has been optimized for expression in lactic acid bacteria (pGnMM119); this construct has the reverse order of EBI3 and IL-12 p35 subunits compared to that in SEQ ID NOs: 1 and 2. Within SEQ ID NO: 10:

| Positions | |
|---|---|
| 1-16 | cloning site |
| 17-22 | Shine-Dalgarno sequence |
| 23-30 | spacer |
| 31-33 | Start codon |
| 31-120 | encode usp45 signal peptide, including its physiological downstream sequence, AspThrAsn (DTN). |
| 121-126 | a NheI restriction site; introduces Ala-Ser in the amino acid sequence. |
| 130-747 | EBI3/IL-27β portion of the engineered, single-chain Murine IL-35 |
| 748-822 | encode a rigid linker. |
| 823-1404 | p35/IL-12α portion of the engineered, single-chain Murine IL-35. |
| 1402-1404 | stop codon. |
| 1-6 and 1405-1424 | restriction sites used for cloning. |

SEQ ID NO: 11 is the amino acid sequence of the single-chain murine IL-35 encoded by SEQ ID NO: 10. Within SEQ ID NO: 11

| Positions | |
|---|---|
| 1-30 | usp45 signal peptide (positions 1-27), including its physiological downstream sequence AspThrAsn (DTN; positions 28-30). |
| 31-32 | Ala-Ser resulting from inclusion of a NheI restriction site upstream of p35. This site facilitates eventual mending intervention(s) that may have been needed. |
| 34-239 | EBI3/IL-27β portion of the engineered, single-chain Murine IL-35. |
| 240-264 | a rigid linker. |
| 265-457 | p35/IL-12α portion of the engineered, single-chain Murine IL-35. |

DETAILED DESCRIPTION

Detailed descriptions of one or more preferred embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

The following description includes information that may be useful in understanding the present disclosure. It is not an admission that any of the information provided herein is prior art, or that any publication specifically or implicitly referenced is prior art.

Unless defined otherwise, all technical and scientific terms used herein have the same meaning as commonly understood by one of ordinary skill in the art to which this disclosure belongs.

As used herein, the term "adjuvant" refers to a substance sometimes included in a vaccine or therapeutic formulation to enhance or modify the immune-stimulating properties of the vaccine or therapeutic formulation.

As used herein, the term "antigen" refers to a substance that triggers an immune system response, resulting in production of an antibody specific for the antigen. Thus, an antigen is a substance that binds specifically to a respective antibody.

As used herein, the term "operon" refers to a cluster or series of adjacent structural genes that are transcribed as a unit into a single mRNA molecule. The cluster or series of adjacent structural genes can be under the control of a single promoter and also under the control of a composite tandem promoter.

As used herein, the term "autoimmune disease" refers to a physiological condition in a subject that is resultant from the subject's own body producing an inappropriate immune response that targets and damages the subject's own cells.

As used herein, the term "inflammatory disease" or "inflammatory condition" encompasses any disease or condition characterized by inflammation. Inflammation is a basic physiological response to a variety of external or internal insults, such as infectious agents, physical injury, hypoxia, or disease processes. Therefore, diseases or conditions falling within "inflammatory disease" do not have to share a common genetic or physiological basis, so long as the disease or condition results in inflammation. Representative conditions that are encompassed in the term inflammatory disease include allergies, alopecia areata, anemia, aphthous ulcer, arthritis (such as rheumatoid, juvenile rheumatoid, psoriatic, and gouty arthritis, and osteoarthritis), asthma (including allergic asthma), celiac disease, Crohn's disease, dermatitis (including atopic dermatitis and eczematous dermatitis), diabetes, diabetes mellitus, Hashimoto's thyroiditis, irritable bowel disease, cutaneous and systemic lupus erythematosus, multiple sclerosis, myasthenia gravis, osteoporosis, psoriasis, scleroderma, Sjogren's syndrome (including keratoconjunctivitis sicca secondary to Sjogren's syndrome), other endocrinopathies, ulcerative colitis, vaginitis and Wegener's granulomatosis.

As used herein, the term "recombinant bacteria" refers to bacteria that have been genetically modified from their native state. For instance, recombinant bacteria may have nucleotide insertions, nucleotide deletions, nucleotide rearrangements, and nucleotide modifications introduced into the bacterial DNA. Further, recombinant bacteria may include exogenous nucleotide sequences on plasmids or exogenous nucleotide sequences stably incorporated into the chromosomal DNA.

As used herein, and in light of the previous definition, the term "recombinant lactic acid bacterial cell" refers to lactic acid bacterial cells that have been genetically modified from their native state. In some aspects of the disclosure, for example, a "recombinant lactic acid bacterial cell" includes exogenous nucleotide sequences from a mammal or other animal.

As used herein, the term "probiotic microorganism" is a microorganism which has a beneficial effect on a host's intestinal microflora ecology, presumably by promoting the growth of so-called "good" microorganisms, inhibiting the growth of so-called "bad" microorganisms, or by performing metabolic activities that are beneficial to the host. In particular embodiments herein, the disclosed recombinant bacteria perform metabolic functions that are beneficial to a host. In certain embodiments, the recombinant bacteria are lactic acid bacteria, a common probiotic bacterial clade.

There is an ongoing need in the art for the development of safe, bacterial based therapeutics that are not reliant upon attenuated invasive bacterial strains and therefore do not suffer from the aforementioned drawbacks. Specifically, the development of a Gram-positive delivery system for expressing engineered, single-chain mammalian IL-35, in a bacterial species that has been accorded a Generally Recognized as Safe (GRAS) status, would offer consumers suffering from autoimmune and inflammatory disease a superior delivery system for expressing engineered, single-chain mammalian IL-35.

Many mammalian pathogens invade the host through a mucosal surface and arm the mucosa to ultimately prevent pathogens from initiating infection. The mucosa is also the site where many environmental and food antigens are processed. Mucosal immunity, be it to combat pathogens or to maintain tolerance, is accomplished by facilitating vaccine uptake to mucosal inductive tissues. Similarly, non-pathogen or "good" bacteria (such as probiotics) release proteins that are then taken up by the mucosal tissues to induced tolerance, or to down-modulate the immune response, allowing these beneficial bacterial to reside in the intestinal tract without immune activation.

Mucosal inductive sites are present in the gut known as Peyer's patches, and in the upper respiratory tract referred to as nasal-associated lymphoid tissues (NALT) or in humans, referred to as Waldeyer's ring (tonsils and adenoids). At such inductive sites, foreign proteins or materials (e.g., antigens), are sampled and used to trigger a host immune response.

Once proteins are sampled and processed, they will induce memory lymphocyte responses in mucosal tissues, which are the various mucosal surfaces of the gut, respiratory tract, and genitourinary tract. These mucosal effector sites contain naïve and memory B and T lymphocytes, antigen presenting cells (APCs), as well as a plethora of other cell types with different functions in the mucosal network that ultimately determines the outcome of the immune response.

Without wishing to be bound to a particular theory, the present inventors hypothesize that some, but not all, of the molecules that pathogens transfer to target cells may at the same time down-regulate the immune system. In the present disclosure, the inventors have shown that this is correct, and when applied appropriately this discovery leads to the development of novel therapeutic compositions that are useful for the treatment of autoimmune disorders and inflammatory disease.

As described herein, the inventors have exploited a recombinant *Lactococcus lactis* to express an engineered, single-chain mammalian IL-35, that when orally delivered to mice, is able to prevent the symptoms and to block the progression of collagen-induced arthritis (CIA). CIA is a recognized model of rheumatoid arthritis and therefore implicates the ability of the recombinant bacteria taught herein to be an effective treatment for this highly pervasive autoimmune disease.

Thus, the present inventors have illustrated that the recombinant *Lactococcus lactis* expressing an engineered, single-chain mammalian IL-35 protein have strong potential to act as multi-purpose modulators of pathological immune response in absence of an autoantigen.

These discoveries have profound implications for the treatment and prevention of autoimmune diseases like rheumatoid arthritis and other inflammatory diseases.

Lactic Acid Bacteria

The disclosure herein demonstrates that engineered, single-chain mammalian IL-35 can be successfully expressed in a Gram-positive bacterial vector system. That is, the disclosure presents a lactic acid bacterium, *Lactococcus lactis*, which includes an engineered plasmid containing a nucleotide sequence encoding an engineered, single-chain mammalian IL-35. The nucleotide sequence is shown to be expressed in the *Lactococcus lactis* system.

Lactic Acid Bacteria Classification

The lactic acid bacteria include a clade of Gram-positive bacteria associated by their common metabolic and physiological characteristics. For instance, these bacteria have low-GC, are acid-tolerant, are generally non-sporulating and non-respiring, rod-shaped bacilli or cocci phenotypes. As their name implies, lactic acid bacteria produce lactic acid as the major metabolic end-product of carbohydrate fermentation.

The order Lactobacillales includes the lactic acid bacteria. Families present in the Lactobacillales include: Aerococcaceae, Carnobacteriaceae, Enterococcaceae, Lactobacillaceae, Leuconostocaceae, and Streptococcaceae. A representative genus of Streptococcaceae is *Lactococcus*. A representative species of *Lactococcus* is *Lactococcus lactis*.

The aforementioned is not an exhaustive list of the members of the lactic acid bacteria but is merely illustrative of the structuring of the group. One of skill in the art would be able to ascertain the members of the lactic acid bacteria.

The present disclosure utilizes *Lactococcus* bacteria in the exemplary embodiments, but it would be within the skill of one in the art to utilize the taught methods for expression of the provided engineered, single-chain mammalian IL-35 in other lactic acid bacteria. For example, the disclosed promoter sequences along with the taught signal sequence coding regions (encoding the signal sequence peptides) are engineered for lactic acid bacteria and would be useful for deployment in other lactic acid bacterial species.

One of skill in the art would be able to utilize the disclosed methods to insert the engineered, single-chain mammalian IL-35 structural gene sequence, with appropriate signal sequence coding regions for the particular lactic acid bacterial recipient, into a recipient lactic acid bacterial cell and obtain expression of an engineered, single-chain mammalian IL-35. The ascertainment of the appropriate signal sequence coding regions would be ascertainable based upon the particular lactic acid bacterial species that would be receiving the engineered, single-chain IL-35 structural gene sequence.

Also appropriate for use in the methods and compositions described herein are probiotic Bacilli, such as strains of *Bacillus subtilis*. *B. subtilis* is a Gram-positive, nonpathogenic, spore-forming organism; the robustness of its spores is thought to enable passage across the gastric barrier, whereby the spores germinate in the small intestine and transiently populate it. Probiotic strains of *B. subtilis* have long been used for oral bacteriotherapy and bacterioprophylaxis for gastrointestinal disorders (Mazza, *Boll Chim Farm.* 133(1):3-18, 1994; Tompkins et al., *Benef Microbes.* 1(1): 93-106, 2010). Spores of *B. subtilis* are extremely resistant and stable, easy to manipulate and are known to interact with immune cells inducing protective, antigen-specific immune responses. Furthermore, *B. subtilis* has outstanding biotechnological potentials including ease of manipulation, high-protein production and secretion (Song et al., *J Microbiol Biotechnol.* 25(7):963-77, 2015).

Lactic Acid Bacteria Benefits

There are several benefits to utilizing lactic acid bacteria to host and deliver the engineered, single-chain mammalian IL-35.

First, lactic acid bacteria do not present lipopolysaccharide complex (LPS) that is associated with the outer membrane of, for instance, a *Salmonella* based vector.

Second, lactic acid bacteria do not present a problem with reversion to a virulent state, because lactic acid bacteria are not virulent. In fact, they have a Generally Recognized as Safe (GRAS) status. GRAS status is a Food and Drug Administration designation that a chemical or substance added to food is considered safe by experts, and thus is exempted from the usual Federal Food, Drug, and Cosmetic Act food additive tolerance requirements.

Third, there is an insignificant risk of horizontal gene transfer to other invasive bacteria as would be more prevalent with a Gram-negative vector (such as *Salmonella*).

Furthermore, the taught lactic acid bacteria vectors offer several distinct advantages over a *Salmonella* vector.

For instance, lactic acid bacteria have a long history of beneficial association with human intestinal microflora. Thus, the use of lactic acid bacteria offers the opportunity to create synergistic effects between recombinant lactic acid bacteria expressing an engineered, single-chain mammalian IL-35 and other resident intestinal microbial flora.

Consider that probiotics are products aimed at delivering living, potentially beneficial, bacterial cells to the intestinal ecosystem of humans and other animals. Strains of lactic acid bacteria are the most common microbes employed as probiotics (Sonomoto & Yokota, *Current Progress in Advanced Research.* Caister Academic Press. ISBN 978-1-904455-82-0 2011). This presents the opportunity to utilize the herein described lactic acid bacteria expressing engineered, single-chain mammalian IL-35 in compositions that also include probiotic bacterial strains such as those from the genus *Lactobacillus* and *Bifidobacterium*.

As will be illustrated in the disclosed Examples, the present recombinant *Lactococcus lactis* strains expressing engineered, single-chain mammalian IL-35 also demonstrate potency.

IL-35

Produced by Tregs (Kochetkova et al., *J. Immunol.* 184: 7144-7153, 2010; Collison, et al., *Nature* 450:566-571, 2007; Niedbala et al., *Eur. J. Immunol.* 37: 3021-3029, 2007), IL-35 can potently suppress arthritis (Kochetkova et al., *J. Immunol.* 184:7144-7153, 2010; Niedbala et al., *Eur. J. Immunol.* 37: 3021-3029, 2007; Nakano et al., Rheumatology (Oxford). 54(8):1498-506, 2015), colitis (Collison, et al., *Nature* 450:566-571, 2007; Wirtz et al., *J. Gastroenterol.* 141:1875-1886, 2011), Sjögren's syndrome (Guo et al., *Scand J Immunol.* 88(5):e12718, 2018), atherosclerosis (Park et al., *J Biol Chem.* 291(7):3359-70, 2016), type 1 diabetes (Bettini et al., *Diabetes.* 61(6):1519-26, 2012; Manzoor et al., *Eur J Immunol.* 47(1):144-154, 2017; Manzoor et al., *Eur J Immunol.* 47(1):144-154, 2017) and EAE (Collison, et al., *Nat. Immunol.* 11:1093-1101, 2010; Duffy et al., *J Neurosci.* 39(12):2326-2346, 2019). IL-35 is also important for maintaining peripheral immune tolerance during pregnancy (Liu et al., *Exp Cell Res.* 111513, 2019).

Humans produce IL-35, and its inhibitory effect is contact-independent (Chaturvedi et al., *J. Immunol.* 186:6661-6666, 2011). Since IL-35 can mediate its effects via the stimulation of IL-10 (Kochetkova et al., *J. Immunol.* 184: 7144-7153, 2010; Niedbala et al., *Eur. J. Immunol.* 37: 3021-3029, 2007; Collison et al., *J. Immunol.* 182:6121-6128, 2009) and TGF-β (Kochetkova et al., *J Immunol.* 192(2):804-16, 2014), as well as perpetuating itself, it has profound capacity for immunoregulation dampening innate and adaptive immune responses. Thus, limited use of IL-35 offers an attractive alternative to remedy autoimmunity.

Prior to the current work, IL-35 has proved difficult to work with. For instance, Huang et al. (*J Inflamm* (Lond). 14:16, 2017. doi: 10.1186/s12950-017-0164-5) describes difficulties of producing recombinant IL-35. Expression in *E. coli* leads to non-functional protein (Aparicio-Siegmund et al., *PLoS One.* 9(9):e107990, 2014). Experience of the present inventors, gained in part while generating data for Kochetkova et al. (*J Immunol.* 184:7144-53, 2010), confirms that IL-35 is laborious and costly to produce in yeast. The clear difficulty in working with IL-35 is also indirectly supported when considering the tremendous anti-inflammatory properties of IL-35, coupled with the scarcity of papers describing related translational research.

Functional IL-35 has been produced in insect cells (Wang et al., *Nat Med.* 20:633-41, 2014), but their approach is hampered by the need to purify the recombinant protein. The herein-described approach, which uses *Lactococcus* both as a microbial cell factory and a delivery agent, is more effective and reduces production costs by 95-99%.

Producing the two subunits of IL-35, p35 and EBI3, as separate proteins introduces the hurdle of the physical interaction of the two subunits. One of the mechanisms believed to regulate the low in vivo concentration of heterodimeric IL-35 is that the EBI3 sub-unit is sequestered and degraded in the endoplasmic reticulum (Devergne et al., *J Virol.* 70(2):1143-53, 1996). The herein-described system for producing IL-35 as a holoprotein rather than a bicistronic construct has effectively overcome this issue.

The anti-inflammatory role of IL-35 has been demonstrated in rodents and humans. Among mammals, p35 and EBI3 show some sizeable, but not stringent, amino acid identity. As an example, mouse and human p35 (GenBank Accession Nos. AAL01442.1 and NP_000873.2, respectively) and EBI3 (GenBank Accession Nos. NP_056581.1 and ABK41923.1, respectively) have a 58% and 64% identity, respectively. It is therefore expected that IL-35 may function better when it is species-matched, or used in closely related species.

Thus, provided herein are engineered murine-derived IL-35 constructs (e.g., SEQ ID NOs: 1 and 2, 10 and 11) that are particularly useful in embodiments involving rodent subjects. Similarly, there are provided engineered canine-derived IL-35 constructs (e.g., SEQ ID NOs: 4 and 5), which are particularly useful in embodiments involving canine subjects. Finally, there are provided herein engineered human-derived IL-35 constructs (e.g., SEQ ID NOs: 6 and 7), which are particularly useful in embodiments involving human and other primate subjects.

Also specifically contemplated are constructs in which the order of the p35 and EBI3 subunits in the construct is reversed—that is, though SEQ ID NOs: 2, 6, and 7 are provided with the subunits in the order P35-then-EBI3, also completed are single chain IL-35 constructs in which the subunits are in the order EBI3-then-p35 (exemplified herein in SEQ ID NO: 11). Thus, also specifically contemplated are engineered human and canine single-chain IL-35 fusions in which the subunits are in the order EBI3-then-p35. Though usually the provided single-chain IL-35 fusion proteins will originate from the same mammal (e.g., both from human, canine, or murine origin), also contemplated are single-chain fusions in which the p35 (IL-12α) subunit is of human original while the EBI3 (IL-27β) subunit is of canine or murine origin—or vice versa, in all of the available combinations.

Also contemplated are functional variants of the provided nucleic acid and amino acid sequences. Such functional variants include nucleic acids (e.g., gene, pre-mRNA, mRNA) and polypeptides, polymorphic variants, alleles, mutants, and interspecies homologs that: (1) have an amino acid sequence that has at least 80%, 85%, 87%, 90%, 91%, 92%, 93%, 94%, 95%, 96%, 97%, 98% or 99% or greater amino acid sequence identity, preferably over a region of over a region of at least 25, 50, 100, 200, 300, 400, or more amino acids, to a polypeptide encoded by a respectively referenced nucleic acid or an amino acid sequence; which variant maintains at least one biological function of the single-chain engineered IL-35 as described herein.

The phrase conservatively modified variant(s) applies to both amino acid and nucleic acid sequences. With respect to particular nucleic acid sequences, the phrase 'conservatively modified variants' refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein or protein domain. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one type of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions, or additions to a nucleic acid, peptide, polypeptide, or protein sequence which alters, adds or deletes a single amino acid or a small percentage of amino acids in the encoded sequence is a "conservatively modified variant", where the alteration results in the substitution of an amino acid with a chemically similar amino acid. Conservative substitution tables that provide functionally similar amino acids are well known in the art. Such conservatively modified variants are in addition to and do not exclude polymorphic variants, interspecies homologs, and alleles of the invention. The following eight groups each contain amino acids that are considered conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Described herein are working embodiments that employ a minimalist GPG linker between the two IL-35 subunits; this linker was selected because it presents the low risk of disturbing protein function. The GPG linker includes two glycines, which allow for unhindered swiveling; and a proline that acts as a "circuit-breaker", preventing secondary structures to spill into neighboring protein domains. Alternative configurations and modification(s) of the linker are contemplated as useful in the current invention. There are three categories of linkers: 1) flexible, 2) rigid, 3) cleavable. Each design has pros and cons (reviewed in Chen et al., *Adv Drug Deliv Rev.* 65(10):1357-69, 2013, for instance), and linker optimization is within the skill of the ordinary artisan. Such optimization can readily be carried out on a case-by-case basis. Additional contemplated linkers included, for instance, $(GGGGS)_3$ (corresponding to positions 230-245 of SEQ ID NO: 7; three serial repetitions of SEQ ID NO: 9), the rigid linker corresponding to positions 240-264 of SEQ ID NO: 11, and another rigid peptide linker AEAAAKEAAAKA (SEQ ID NO: 8). Contemplated herein are engineered mammalian single chain IL-35 proteins that use a rigid linker or a flexible linker. Optionally, the linker may be short or long.

Expression of Mammalian IL-35 in Gram-Positive Bacteria

The present disclosure teaches that Gram-positive bacteria expressing engineered, single-chain mammalian IL-35 are therapeutically effective at treating or preventing autoimmune and/or inflammatory disease.

The method of expressing engineered, single-chain mammalian IL-35 in Gram-positive bacteria may include inserting a plasmid carrying an engineered, single-chain IL-35 encoding sequence into a recipient Gram-positive bacterial host.

Further, in some embodiments, the method of expressing an engineered, single-chain mammalian IL-35 in Gram-positive bacteria may include stably integrating the engineered, single-chain IL-35 encoding sequence into the chromosome of a recipient Gram-positive bacterial host.

The term "plasmid" is used to refer to a molecule capable of autonomous replication that is suitable for transformation of a recipient bacterial strain and contains DNA sequences that direct and/or control the expression of inserted heterologous DNA sequences. Various types of plasmids may be used such as low and high copy number plasmids, narrow and broad-host range plasmids, expression plasmids, and cosmids.

In order to prevent loss of the plasmid expressing the engineered, single-chain mammalian IL-35, an element may be added to the plasmid which enhances its stability. Methods for improvement of plasmid stability are known to those in the art.

In general, heterologous gene expression is achieved by cloning of the heterologous gene into a plasmid (such as a representative plasmid described herein), which is replicated within the recipient in multiple copies thus leading to high expression of foreign gene product. Expression of the herein described heterologous sequences encoding an engineered, single-chain mammalian IL-35 are achievable by application of known genetic engineering techniques such as those described in, e.g. Sambrook and Russell (2001) *"Molecular Cloning: A Laboratory Manual* (3rd edition), Cold Spring Harbor Laboratory, Cold Spring Harbor Laboratory Press, New York. It is demonstrated herein that engineered, single-chain mammalian IL-35 may be expressed in Gram-negative bacteria.

The disclosed engineered DNA construct, i.e. a DNA construct including the encoding sequence of any one of SEQ ID NOs: 1, 10, 4, or 6, including a promoter operably linked to DNA encoding the engineered, single-chain mammalian IL-35 may be made and transformed into the Gram-positive bacteria using conventional techniques. Transformants containing the DNA construct may be selected, for example, by screening for a selectable marker on the construct. Bacteria containing the construct may be grown in vitro before being formulated for administration to the host. Selectable markers suitable for the herein described recombinant bacteria would be known to those of skill in the art.

The recombinant bacteria taught herein may include a nucleotide sequence encoding engineered, single-chain mammalian IL-35 that have been codon optimized. "Codon optimization" is defined as modifying a nucleic acid sequence for enhanced expression in the cells of the host bacterial species of interest, e.g. Gram-positive bacteria, by replacing at least one, more than one, or a significant number of codons of the native mammalian IL-35 sequence with codons that are more frequently or most frequently used in the genes of the recipient Gram-positive bacteria.

Various bacterial species exhibit particular bias for certain codons of a particular amino acid and thus codon optimization can ensure optimal expression of the engineered, single-chain mammalian IL-35 in the recipient bacterial host cell being transformed. Codon preference or codon bias is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, the presently disclosed engineered, single-chain mammalian IL-35 encoding sequences can be tailored for optimal gene expression in a given Gram-positive bacteria based on codon optimization.

Working embodiments herein use the Usp45 signal peptide to ensure the single-chain, engineered IL-35 is secreted. However, it is recognized that alternative signal peptides, both natural as well as engineered and/or optimized signal peptides, can be useful in expression constructs of the current invention. The art recognizes many signal peptides that are functional for secreted expression from *Lactococcus lactis* and the like. See, for instance, the teachings in: Ng & Sarkar (*App Environ Microbiol.,* 79(1):347-356, 2013), Le Loir et al. (*App Environ Microbiol.,* 67(9):4119-4127, 2001), Ravn et al. (Microbiology, 149(Pt 8):2193-2201, 2003), Morello et al. (*J Mol Microbiol Biotechnol.* 14:48-58, 2008), and Mahmud et al. (*J Biotechnol.* 296:22-31, 2018).

Optionally, the engineered IL-35 provided herein can be further modified to include a molecular anchor for surface-display. Anchoring and surface-display may directly expose IL-35 to cell-surface receptor(s) either during the sampling process by GI DCs through the mucous layer, or during subsequent trafficking of bacteria. Also, mucosal immunization other than oral (nasal, vaginal, anal, sublingual) may benefit from a facilitated contact between the surface-displayed IL-35 and relevant cell types. (Leenhouts et al., Antonie Van Leeuwenhoek. 76(1-4):367-76, 1999; Michon et al., *Microb Cell Fact.* 15:70, 2016; Cortes-Perez et al., *FEMS Microbiol Lett.* 229(1):37-42, 2003).

Furthermore, this approach may lead to deployment of the GEM (Gram-positive enhanced matrix) technology, whereby the recombinantly-produced protein of interest is engrafted onto a non-viable LAB scaffold, thus bypassing the recombinant regulatory hurdles (van Roosmalen et al., *Methods.* 38(2):144-9, 2006; Sirec et al., *FEMS Microbiol Lett* 358(2):194-201, 2014). The GEM tech also allows for loading more than one functional protein onto the same particles.

Additional components of the herein-described IL-35 expression constructs can be modified or varied, including for instance: the promoter used to express the engineered polypeptide, the construct from which the polypeptide is expressed, whether the construct remains exosomal or integrates into the genome of the host bacteria, and so forth. Representative systems for expressing polypeptides, including therapeutic proteins, in *Lactococcus* bacteria are described for instance, in: Morello et al., *J Mol Microbiol Biotechnol.* 14:48-58, 2008; Plavec & Berlec, *Appl. Microbiol Biotechnol.,* 103(5):2053-2066, 2019; Mierau & Kleerebezem, *Appl. Microbiol Biotechnol.* 68(6):705-717, 2005;

Ng & Sarkar, *App Environ Microbiol.,* 79(1):347-356, 2013; Lim et al., *Microb Cell Fact* 16(1):221, 2017; and other references cited herein.

Formulation of Compositions

The compositions presented herein are suitable for combination with any known pharmaceutically acceptable carrier, buffer, excipient, adjuvant, or mixture thereof.

Pharmaceutically acceptable carriers are well known and are usually liquids, in which an active therapeutic agent is formulated. In the present case, the active therapeutic agent is the disclosed recombinant bacteria expressing an engineered, single-chain mammalian IL-35. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, MD: Lippincott Williams & Wilkins, 2000, the entire contents of which are hereby incorporated by reference, and include saline, water, buffered water, dextrose and the like. Optionally, the compositions provided herein may be lyophilized, with or without stabilizers (such as trehalose), before it is used to produce a formulation.

The compositions presented herein may in some embodiments be placed within foodstuffs, such as: beverages, dairy products, yogurts, fermented food products, and the like, as feasible and consumer friendly delivery vehicles.

The compositions taught herein may also be delivered in food supplements, such as: powdered compositions including the herein described recombinant bacterial cells, encapsulated compositions including the herein described recombinant bacterial cells, or any liquid formulation including the herein described recombinant bacterial cells.

The compositions may include other therapeutically effective agents such as anti-inflammatory cytokines.

The compositions may include other bacterial species, such as those bacterial species commonly referred to as "probiotics." Furthermore, "prebiotics" may also be present in the herein described compositions.

Probiotics are often defined as live microorganisms that when administered in adequate amounts confer health benefits to the host. The compositions of the present disclosure may include probiotic microorganisms in an amount sufficient to at least partially produce a health benefit.

Prebiotics are often defined as food substances that promote the growth of probiotics in the intestines. They are not broken down in the stomach and/or upper intestine or absorbed in the GI tract of the person ingesting them, but they are fermented by the gastrointestinal microflora and/or by probiotics. The prebiotics that may be used in accordance with the present disclosure are not particularly limited and include all food substances that promote the growth of probiotics in the intestines.

Thus, disclosed herein are probiotic compositions including recombinant lactic acid bacteria expressing an engineered, single-chain mammalian IL-35. In certain aspects, the herein described probiotic compositions support a healthy immune system. The herein described probiotic compositions may also be used to supplement an individual's normal dietary regime.

Furthermore, in certain embodiments, the present disclosure teaches dietary supplements that include recombinant bacteria including a nucleotide sequence encoding an engineered, single-chain mammalian IL-35. In particular embodiments, the recombinant bacteria express the engineered IL-35 protein. In certain aspects, the herein described dietary supplements support a healthy immune system. The dietary supplements may also be used to supplement an individual's normal dietary regime.

The present disclosure also teaches food additive compositions that include recombinant bacteria containing a nucleotide sequence encoding an engineered, single-chain mammalian IL-35 protein. In particular embodiments, the recombinant Gram-positive bacteria expresses the engineered, single-chain mammalian IL-35.

In certain aspects, the herein described food additives support a healthy immune system.

The herein described food additive compositions of the disclosure may be directly ingested or used as an additive in conjunction with foods.

It will be appreciated that the disclosed food additives may be incorporated into a variety of foods and beverages including: yogurt, ice cream, cheese, baked products such as bread, biscuits and cakes, dairy and dairy substitute foods, confectionery products, edible oil compositions, spreads, breakfast cereals, juices, and the like.

Heating (e.g., cooking) a product containing gram-positive bacteria expressing IL-35, or simply containing the expressed IL-35, will likely destroy significant IL-35 activity. More specifically, heating is expected to denature the IL-35 polypeptide.

It is believed that lyophilization, with or without a stabilizer (such as trehalose or another disaccharide) is a viable option for processing of IL-35-containing compositions produced using the herein-described technology. The art recognizes that freezing and freeze-drying can be used in the preparation of pharmaceutical formulations. Optionally, the IL-35 is stabilized during such processing; see, for instance, Olsson et al. (*J Phys Chem B.* 120(20):4723-4731, 2016) and Izutsu (*Adv Exp Med Biol.* 1081:371-383, 2018).

Routes of Administration

The herein described compositions may be used for mucosal administration, such as oral, nasal, vaginal, and rectal delivery; as well as topical administration. Particular embodiments of administration include oral administration, intranasal administration, and topical administration (e.g., for treatment of psoriasis or eczema).

In some oral administration embodiments, the compositions include the disclosed recombinant bacteria expressing an engineered, single-chain mammalian IL-35 and optionally other molecules that are dissolved or suspended in a pharmaceutically acceptable, preferably an aqueous carrier. In addition, the composition may contain excipients, such as buffers, binding agents, diluents, flavors, lubricants, etc.

Consumption of LL-IL35 is an effective means to deliver the recombinant IL-35 to the oral cavity and gastrointestinal tract. Hence, such delivery can be applied to treat diseases of the oral cavity as well as the gastrointestinal tract. Once absorbed from the oral cavity or GI tract, the IL-35 may also enter circulation to treat peripheral autoimmune diseases. An advantage of using *Lactococcus lactis* is that it can be used to ferment milk into yogurt, in which the *Lactococcus lactis* are viable and stable for at least two weeks. Such fermentation preserves the *Lactococcus lactis* and extends the lifespan of the therapeutic product.

The engineered lactic acid bacteria provided herein are not only delivery agents, but they are also beneficial because they can be used to produce a palatable, yogurt-like therapeutic composition/formulation. This provides a remarkable innovation in terms of ease and cost of production. More importantly, the redressed therapeutic agent is predicted to improve acceptance by sections of the market that may be uncomfortable with or wary of "pill" medications, particularly for long-terms ailments. Some consumers do not like to be administered pills, but they may perceive an enhanced probiotic product in their refrigerators as more acceptable. However, pills, capsules, and the like are also still contemplated as formulation formats for the therapeutic compounds and compositions provided herein.

Quantitative Administration

The compositions taught herein may include varying amounts of the recombinant bacteria expressing an engineered, single-chain mammalian IL-35. The particular amount of therapeutic bacterial vector present in the composition may depend upon the disease being treated and/or the subject being administered the therapeutic composition.

For instance, factors such as age, gender, ethnicity, genetic disposition to disease, health, weight, etc. may govern the amount/number of recombinant bacteria present in a composition.

The type of disease or condition being treated may also be taken into consideration when determining the optimal amount of recombinant bacterial vector that should be in a given composition.

In some embodiments, a particular amount of the disclosed therapeutic composition including recombinant bacterial cells expressing an engineered, single-chain mammalian IL-35 is defined as "a therapeutically effective amount" or "therapeutically effective dose." This amount represents a quantity of the disclosed compositions that is capable of eliciting an immune response in the recipient. For example, a "therapeutically effective dose" may be capable of increasing the level of an anti-inflammatory cytokine in the recipient. Furthermore, a "therapeutically effective does" may be able to suppress the level of an inflammatory cytokine in the recipient.

In some particular embodiments, a "therapeutically effective dose" increases the level of the regulatory cytokine IL-10 in a subject upon administration of the herein described composition, as compared to the level of IL-10 present in the subject before administration of the herein described composition.

In other embodiments, a "therapeutically effective dose" suppresses the level of at least one of IFN-$\gamma$ or IL-17 upon administration of the herein described composition, as compared to the level of at least one of IFN-$\gamma$ or IL-17 present in the subject before administration of the herein described composition.

Compositions of the present disclosure may include: $1 \times 10^8$ CFU, $2 \times 10^8$ CFU, $3 \times 10^8$ CFU, $4 \times 10^8$ CFU, $5 \times 10^8$ CFU, $6 \times 10^8$ CFU, $7 \times 10^8$ CFU, $8 \times 10^8$ CFUs, $9 \times 10^8$ CFU, $10 \times 10^8$ CFU, $11 \times 10^8$ CFU, $12 \times 10^8$ CFU, $13 \times 10^8$ CFU, $14 \times 10^8$ CFU, $15 \times 10^8$ CFU, $16 \times 10^8$ CFU, $17 \times 10^8$ CFU, $18 \times 10^8$ CFUs, $19 \times 10^8$ CFU, $20 \times 10^8$ CFU, $30 \times 10^8$ CFU, $40 \times 10^8$ CFU, $50 \times 10^8$ CFU, or more of a recombinant bacteria expressing an engineered, single-chain mammalian IL-35.

Further, the compositions may include any range of CFU that is achievable based upon the aforementioned individual concentrations. For example, the compositions may include from $1 \times 10^8$ CFU to $50 \times 10^8$ CFU per treatment.

Further, the compositions may include ranges of: $1 \times 10^6$ to $1 \times 10^{10}$ CFU, or $1 \times 10^6$ to $2 \times 10^{10}$ CFU, or $1 \times 10^6$ to $3 \times 10^{10}$ CFU, or $1 \times 10^6$ to $4 \times 10^{10}$ CFU, or $1 \times 10^6$ to $5 \times 10^{10}$ CFU, or $1 \times 10^6$ to $6 \times 10^{10}$ CFU, or $1 \times 10^6$ to $7 \times 10^{10}$ CFU, or $1 \times 10^6$ to $8 \times 10^{10}$ CFU, or $1 \times 10^6$ to $9 \times 10^{10}$ CFU, or $1 \times 10^6$ to $10 \times 10^{11}$ CFU of a recombinant bacteria expressing an engineered, single-chain mammalian IL-35.

Embodiments of the compositions may include at least $1 \times 10^8$ CFU, or at least $2 \times 10^8$ CFU, or at least $3 \times 10^8$ CFU, or at least $4 \times 10^8$ CFU, or at least $5 \times 10^8$ CFU, or at least $6 \times 10^8$ CFU, or at least $7 \times 10^8$ CFU, or at least $8 \times 10^8$ CFUs, or at least $9 \times 10^8$ CFU, or at least $10 \times 10^8$ CFU, or at least $11 \times 10^8$ CFU, or at least $12 \times 10^8$ CFU, or at least $13 \times 10^8$ CFU, or at least $14 \times 10^8$ CFU, or at least $15 \times 10^8$ CFU, or at least $16 \times 10^8$ CFU, or at least $17 \times 10^8$ CFU, or at least $18 \times 10^8$ CFUs, or at least $19 \times 10^8$ CFU, or at least $20 \times 10^8$ CFU, or at least $30 \times 10^8$ CFU, or at least $40 \times 10^8$ CFU, or at least $50 \times 10^8$ CFU of a recombinant bacteria expressing an engineered, single-chain mammalian IL-35.

In a particular embodiment, the composition includes $5 \times 10^8$ CFU of a recombinant bacteria expressing an engineered, single-chain mammalian IL-35.

In some embodiments, the compositions include from $1 \times 10^6$ to $10 \times 10^{11}$ CFU, or $1 \times 10^6$ to $5 \times 10^{10}$ CFU of a recombinant bacteria expressing an engineered, single-chain mammalian IL-35.

The compositions may be administered once a day, twice a day, three times a day, four times a day, or five times a day to a subject in need of such treatment.

The compositions may also be administered at least once a day, at least twice a day, at least three times a day, at least four times a day, or at least five times a day.

Furthermore, the compositions may be administered on an as needed basis based upon a subject's physiological symptoms, such as pain, swelling, irritation, or discomfort.

Some embodiments include administering the herein described compositions including the recombinant bacteria on a prophylactic bases to a subject that does not presently experience physiological symptoms associated with an autoimmune or inflammatory disease.

In particular embodiments, the compositions may be taken daily as part of a food product delivery vehicle, e.g. yogurt, as part of a daily health regimen.

Collagen Induced Arthritis (CIA) Model

Collagen induced arthritis (CIA), a model of rheumatoid arthritis (RA), can be induced upon immunization with heterologous collagen II (CII) in DBA/1 or C57BL/6 mice or by mAbs to CII combined with LPS. CIA shares with RA several critical characteristics of the disease pathogenesis, including CD4$^+$ T cells' mediated inflammation and extensive cartilage and bone damage, resulting in joint deformities. This similarity permits the use of the CIA model as an investigative tool to test novel approaches for prevention and treatment of RA (Courtenay et al., *Nature* 283:666-668, 1980; Terato et al., *J. Immunol.*, 148: 2103-2108, 1992; Terato et al., *Autoimmun*, 22: 137-147 1995).

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A composition, including: a recombinant lactic acid bacterial cell including a nucleotide sequence encoding an engineered, single-chain mammalian IL-35.
2. The composition of embodiment 1, formulated for treatment of an autoimmune or inflammatory disease.
3. The composition of embodiment 1, wherein the recombinant lactic acid bacterial cell expresses at least one heterologous IL-35 nucleic acid encoding the engineered, single-chain mammalian polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 11, 5, or 6 that has at least 85%, at least 90%, at least 95%, or at least 98% sequence identity to that sequence.

4. The composition of embodiment 1, wherein the recombination lactic acid bacterial cell expresses an engineered, single-chain mammalian IL-35 protein including the amino acid sequence shown in SEQ ID NO: 2 (murine), SEQ ID NO: 5 (canine), or SEQ ID NO: 7 (human) from an engineered, single-chain mammalian IL-35 nucleic acid.

5. The composition of embodiment 4, wherein the engineered, single-chain mammalian IL-35 protein is expressed from a transgene including the nucleotide sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence.

6. The composition of embodiment 1, wherein the recombinant lactic acid bacterial cell is a cell from the genus *Lactococcus*.

7. The composition of embodiment 1, wherein the composition induces an anti-inflammatory response in a subject treated with the composition.

8. The composition of any of the above embodiments, wherein the nucleotide sequence encoding the engineered, single-chain mammalian IL-35 is integrated into the genome of the recombinant lactic acid bacterial cell.

9. The composition of any one of the above embodiments, which is a milk-based nutraceutical.

10. The composition of embodiment 9, wherein the milk-based nutraceutical is a fermented milk product.

11. The composition of embodiment 10, wherein the fermented milk product includes a yogurt, a buttermilk, a kefir, a cheese, a crème fraiche, or a cultured sour cream.

12. Use of the composition of any one of embodiments 1-11 for treating an inflammatory disease or condition.

13. The use of embodiment 12, wherein the inflammatory disease or condition includes one or more of an allergy, asthma, autoimmune arthritis, celiac disease, Crohn's disease, diabetes, multiple sclerosis, systemic lupus erythematosus, Sjogren's syndrome, Hashimoto's thyroiditis, and/or another endocrinopathy.

14. Use of the composition of any one of embodiments 1-11 for stimulating IL-10 and TGF-β-producing CD39+ regulatory T cells.

15. Use of the composition of any one of embodiments 1-11 for stimulating one or more regulatory cell subsets including Foxp3 (FOXP3)$^+$ and Foxp3 (FOXP3)$^-$ T cells, CD25$^+$ and CD25$^-$ T cells, regulatory B cells, and regulatory innate cells involved in producing a tolerogenic condition.

16. A recombinant lactic acid bacterial cell, including: a nucleotide sequence encoding an engineered, single-chain mammalian IL-35.

17. The recombinant lactic acid bacterial cell of embodiment 16, wherein the cell expresses at least one heterologous IL-35 nucleic acid encoding the engineered, single-chain mammalian polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 11, 5, or 6 that has at least 85%, at least 90%, at least 95%, or at least 98% sequence identity to that sequence.

18. The recombinant lactic acid bacterial cell of embodiment 16, wherein the recombinant lactic acid bacterial cell expresses SEQ ID NO: 2 (murine), SEQ ID NO: 11 (murine), SEQ ID NO: 5 (canine), or SEQ ID NO: 7 (human) from an engineered, single-chain mammalian IL-35 nucleic acid.

19. The recombinant lactic acid bacterial cell of embodiment 16, wherein the nucleotide sequence encoding the engineered, single-chain mammalian IL-35 includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence.

20. The recombinant lactic acid bacterial cell of embodiment 16, wherein the recombinant lactic acid bacterial cell is a cell from the genus *Lactococcus*.

21. The recombinant lactic acid bacterial cell of any of embodiments 16-20, wherein the nucleotide sequence encoding the engineered, single-chain mammalian IL-35 is integrated into the genome of the recombinant lactic acid bacterial cell.

22. A milk-based nutraceutical composition including: a recombinant lactic acid bacterial cell including a nucleotide sequence encoding an engineered, single-chain mammalian IL-35.

23. The composition of embodiment 22, wherein the recombinant lactic acid bacterial cell expresses at least one heterologous nucleic acid encoding the engineered, single-chain mammalian IL-35 polypeptide that includes the amino acid sequence shown in SEQ ID NO: 2 (murine), SEQ ID NO: 11 (murine), SEQ ID NO: 5 (canine), SEQ ID NO: 7 (human), or a functionally equivalent variant of one of SEQ ID NO: 2, 11, 5, or 6 that has at least 85%, at least 90%, at least 95%, or at least 98% sequence identity to that sequence.

24. The milk-based nutraceutical composition of embodiment 22, wherein the engineered, single-chain mammalian IL-35 includes the amino acid sequence of SEQ ID NO: 2 (murine), SEQ ID NO: 11 (murine), SEQ ID NO: 5 (canine), or SEQ ID NO: 7 (human).

25. The milk-based nutraceutical composition of embodiment 22, wherein the nucleotide sequence includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence.

26. The milk-based nutraceutical composition of embodiment 25, wherein the nucleotide sequence includes the sequence of SEQ ID NO: 1 (murine), SEQ ID NO: 10 (murine) SEQ ID NO: 4 (canine), or SEQ ID NO: 6 (human).

27. Use of the milk-based nutraceutical composition of embodiment 22-26 for treating an inflammatory disease or condition.

28. The use of embodiment 27, wherein an inflammatory disease or condition includes one or more of an allergy, asthma, autoimmune arthritis, celiac disease, Crohn's disease, diabetes, multiple sclerosis, systemic lupus erythematosus, Sjogren's syndrome, Hashimoto's thyroiditis, and/or another endocrinopathy.

29. Use of the milk-based nutraceutical composition of embodiment 22-26 for stimulating IL-10 and TGF-β-producing CD39+ regulatory T cells.

30. Use of the milk-based nutraceutical composition of embodiment 22-26 for stimulating one or more regulatory cell subsets including Foxp3 (FOXP3)$^+$ and Foxp3 (FOXP3)$^-$ T cells, CD25$^+$ and CD25$^-$ T cells, regulatory B cells, and regulatory innate cells involved in producing a tolerogenic condition.

31. A method for treating or preventing an autoimmune or inflammatory disease in a subject, including: administering to the subject the composition of any one of embodiments 1-11 or a composition including the recombinant lactic acid bacterial cell of any one of embodiments 16-21.

32. The method of embodiment 31, wherein the level of IL-10 in the subject is increased upon the administering, as compared to the level of the IL-10 present in the subject before the administering.

33. The method of embodiment 31, wherein the level of TGF-β in the subject is increased upon the administering, as compared to the level of the TGF-β present in the subject before the administering.

34. The method of embodiment 31, wherein the level of at least one of IFN-γ or IL-17 is decreased upon the administering, as compared to the level of at least one of IFN-γ or IL-17 present in the subject before the administering.

35. The method of embodiment 1, wherein the level of TNF-α is decreased upon the administering, as compared to the level of TNF-α present in the subject before the administering.

36. A method for producing a composition for the treatment of an autoimmune or inflammatory disease, including: introducing a nucleotide sequence encoding an engineered, single-chain mammalian IL-35 into a recipient lactic acid bacterial cell.

37. The method of embodiment 36, wherein the engineered, single-chain mammalian IL-35 expresses at least one engineered, single-chain mammalian IL-35 including the amino acid sequence of SEQ ID NO: 2 (murine), SEQ ID NO: 11 (murine), SEQ ID NO: 5 (canine), SEQ ID NO: 7 (human) or a functionally equivalent variant of one of SEQ ID NO: 2, 11, 5, or 6 that has at least 85%, at least 90%, at least 95%, or at least 98% sequence identity to that sequence.

38. The method of embodiment 36, wherein the nucleotide sequence includes the sequence of positions 31-1371 of SEQ ID NO: 1, positions 25-1332 of SEQ ID NO: 10, positions 25-1332 of SEQ ID NO: 4, positions 31-1395 of SEQ ID NO: 6, or a functionally equivalent variant thereof that has at least 85%, at least 90%, at least 95%, or at least 98% sequence identity to that sequence.

39. The method of embodiment 38, wherein nucleotide sequence includes the sequence of SEQ ID NO: 1 (murine), SEQ ID NO: 10 (murine), SEQ ID NO: 4 (canine), or SEQ ID NO: 6 (human).

40. The method of embodiment 36, further including: culturing the lactic acid bacterial cell under conditions which allow for expression of the engineered, single-chain mammalian IL-35.

41. The method of embodiment 36, wherein introducing the nucleotide sequence encoding the engineered, single-chain mammalian IL-35 includes integrating the encoding sequence into the genome of the recipient lactic acid bacterial cell.

Example 1: Delivery of IL-35 by *Lactococcus Lactis*

Ameliorates Collagen-Induced Arthritis in Mice

IL-35, a relatively newly discovered cytokine belonging to the larger IL-12 family, shows unique anti-inflammatory properties, believed to be associated with dedicated receptors and signaling pathways. IL-35 plays a pivotal role in the development and the function of both regulatory B (Bregs) and T cells (Tregs). In order to further its therapeutic potential, a dairy *Lactococcus lactis* strain was engineered to express an engineered, single-chain murine IL-35 (LL-IL35), and this recombinant strain was applied to suppress collagen-induced arthritis (CIA). Oral administration of LL-IL35 effectively reduced the incidence and disease severity of CIA. When administered therapeutically, LL-IL35 abruptly halted CIA progression with no increase in disease severity by reducing neutrophil influx into the joints. LL-IL35 treatment reduced IFN-γ and IL-17 3.7- and 8.5-fold, respectively, and increased IL-10 production compared to diseased mice. Foxp3$^+$ and Foxp3$^-$ CD39$^+$ CD4$^+$ T cells were previously shown to be the Tregs responsible for conferring protection against CIA. Inquiry into their induction revealed that both CCR6$^+$ and CCR6$^-$ Foxp3$^{+\ or\ -}$ CD39$^+$ CD4$^+$ T cells act as the source of the IL-10 induced by LL-IL35. Thus, this example demonstrates the feasibility and benefits of engineered probiotics, and in particular *Lactococcus* expressing an engineered, single-chain mammalian IL-35 protein, for treating autoimmune diseases. At least some of the material contained in this Example was published as Maddaloni et al. (*Frontiers in Immunology*, 9: Article 2691, 2018; doi:10.3389/fimmu.2018.02691).

Materials and Methods

Bacterial Strain Engineering and Maintenance: *Lactococcus lactis* subsp. *lactis* IL1403 (IL1403) was grown on M17 plus 0.5% glucose (M17G). Initial attempts to express IL-35 under the control of the constitutive p23 promoter yielded only rearranged, nonfunctional clones which confirmed the notion that IL-35 is difficult to express and to stabilize in a wide panel of hosts (unpublished observations; Huang et al., *J Inflamm* (Lond). 14:16, 2017; Kochetkova et al., *J Immunol*. 184(12):7144-53, 2010).

To express IL-35, a synthetic gene (SEQ ID NO: 1) codon-optimized for LL was designed in-house and then synthesized by GenScript (Piscataway, NJ). The fragment contains an optimal Shine-Dalgarno sequence properly spaced from the ATG start codon, the usp45 secretion signal, the p35 coding region, a short flexible linker, the EBI3 coding region, and AgeI and SmaI sites at both ends. The fragment was excised with AgeI, gel-purified and cloned into pMSP3535H3 (Kleinewietfeld et al., *Blood* 105(7): 2877-86, 2005; a kind gift of Dr. DA Mills, University of California, Davis) yielding a construct named pBzMM150 (LL-IL35). Expression was achieved under the control of the nisin-inducible promoter (SEQ ID NO: 3) borne on the vector. The expressed single-chain IL-35 protein has the sequence shown in SEQ ID NO: 2.

Collagen-induced Arthritis (CIA): All the animal experiments described in the present study were conducted in strict accordance with the recommendations in the *Guide for the Care and Use of Laboratory Animals* of the National Institutes of Health. All animal studies were conducted under protocols approved by Montana State University's and the University of Florida's Institutional Animal Care and Use Committee.

C57BL/6 males (B6; 8- to 10-weeks of age; Charles River Laboratories, Horsham, PA USA) were maintained at Montana State University Animal Resources Center or the University of Florida Animal Center Services. Groups of B6 males were induced with CIA using 100 µg of chicken collagen II (CII; Chondrex, Redmond, WA USA) emulsified in complete Freund's adjuvant (CFA) and administered s.c. as previously described (Kochetkova et al., *J Immunol.* 184(12):7144-53, 2010; Kochetkova et al., *J. Immunol.* 187: 4654-4666, 2011; Kochetkova et al., *J Immunol.* 192(2): 804-16, 2014). To treat CIA, mice were first orally gavaged with sterile 50% saturated sodium bicarbonate solution to neutralize stomach acidity, followed by $5\times10^8$ CFUs of LL vector or LL-IL35, or vehicle only, sterile PBS. Two dosing regimens were tested, three doses administered on days 14, 21, and 28, and two doses given on days 18 and 25 post-CII challenge. Clinical scores were measured in a double-blind fashion after treatment, and mice were monitored to day 40. Each of the four limbs was evaluated using a scale of 0-3 (Kochetkova et al., *J Immunol.* 184(12):7144-53, 2010; Kochetkova et al., *J. Immunol.* 187: 4654-4666, 2011; Kochetkova et al., *J Immunol.* 192(2):804-16, 2014): 0, no clinical signs; 1, mild redness of a paw or swelling of single digits; 2, significant swelling of ankle or wrist with erythema; 3, severe swelling and erythema of multiple joints; maximum score per mouse is 12.

Cytokine ELISA: CD4+ T cells were cell-sorted by negative selection on magnetic beads (Invitrogen, Grand Island, NY USA) from axillary, popliteal, and inguinal lymph nodes (LNs) yielding purity >98%. Purified CD4+ T cells ($3\times10^6$/ml) were restimulated with 5 µg/ml plate-bound anti-CD3 mAb (eBioscience, San Diego, CA USA) plus 5 µg/ml of soluble anti-CD28 mAb (eBioscience) for 48-72 hrs at 37° C. and 5% $CO_2$ similar to that previously described (Kochetkova et al., *J Immunol.* 184(12):7144-53, 2010). Culture supernatants were collected for cytokine-specific ELISAs (Kochetkova et al., *J Immunol.* 184(12):7144-53, 2010; Kochetkova et al., *J. Immunol.* 187: 4654-4666, 2011; Kochetkova et al., *J Immunol.* 192(2):804-16, 2014).

Flow Cytometry: Splenic and LN cells were stained with fluorochrome-labeled mAbs to CD4, CD39, Ly-6G, Ly-6C, CD11b, and Foxp3 (eBioscience, San Diego, CA), TGF-ß (R&D Systems, Minneapolis, MN USA), and fluorochrome-conjugated streptavidin (BD Pharmingen, San Jose, CA USA). For flow cytometry of Tregs, whole splenic and LN cells ($5\times10^6$/ml culture) were restimulated overnight with 50 µg/ml of CII (T-Cell Proliferation; Chondrex). The next day, cells were stimulated with 25 ng/ml PMA and 1 µg/ml ionomycin for an additional 3 hrs. Cells were harvested, washed, stained and analyzed as previously described (Kochetkova et al., *J Immunol.* 184(12):7144-53, 2010; Kochetkova et al., *J. Immunol.* 187: 4654-4666, 2011; Kochetkova et al., *J Immunol.* 192(2):804-16, 2014).

To measure inflammatory cells in the arthritic joints, isolated limb joints were digested with 2 mg/ml collagenase (*Clostridium histolyticum*, Type IV; Sigma-Aldrich, St. Louis, MO) for 30 min at 37° C., and cell suspensions passed through a 70 µm cell strainer similar to that previously described (Maddaloni et al., *PLoS One.* 10(1): e0117825, 2015; Rampersad et al., *PLoS One* 6(10):e25833, 2011). Leukocytes were stained and analyzed by forward and side-scatter plots for Ly-6G+ Ly-6C+ CD11b+ neutrophils.

Statistics: Mann-Whitney U test was applied to statistically analyze clinical scores. The difference in arthritis incidence between experimental groups was checked with Fisher's exact probability test. One-way ANOVA was performed to analyze ELISA and flow cytometry results. Data were considered statistically significant, if p-value was <0.05.

Results and Discussion

RA is a chronic, systemic autoimmune disorder affecting millions of patients in the US. Treatment of this progressive, degenerative disease demands constant use of anti-inflammatory drugs and often immunosuppressive treatments that increase susceptibility to infections and neoplasia (Carmona et al., *Best Pract. Res. Clin. Rheumatol.* 24: 733-745, 2010; Rosenblum & Amita, *Autoimmun. Rev.* 10: 563-568, 2011; Keyser, *Curr. Rheumatol. Rev.* 7: 77-87, 2011).

Instead, intervention strategies that focus on redirecting or reeducating T cell responses to produce tolerance instead of inflammation have the potential of being a superior treatment for RA.

To address the void for such tolerance induction, it was theorized that a probiotic LAB engineered to express the potent anti-inflammatory cytokine, IL-35 (FIG. 1A), would diminish arthritis. Expression of IL-35 by LL-IL35 was detected by Western blot analysis using a rabbit polyclonal serum against an MBP-IL-35 fusion protein (produced in-house; Kochetkova et al., *J Immunol.* 192(2):804-16, 2014). To test the therapeutic properties of LL-IL35, mice were challenged on day 0 with CII to induce CIA. Given its similarity, CIA is often exploited as an investigative tool to test novel strategies and therapeutics to prevent and treat RA. These mice were randomly divided into three groups for oral treatment: LL-IL35 (pBzMM150), LL vector (pMSP3535H3), or sterile PBS. Two treatment paradigms were tested: beginning intervention on day 14 resembling *Salmonella*-CFA/I treatment (Kochetkova et al., *J. Immunol.* 187: 4654-4666, 2011) with two additional doses on days 21 and 28 (FIG. 1B) or beginning intervention at disease onset on day 18, followed by a second dose on day 25 (FIG. 1C). Clinical scores were performed in double blind, and followed until day 39 post-induction. Changes in disease severity beyond 39 days post-CII challenge are generally not seen.

Using the three-dose regimen, 50% of the LL-IL35-treated mice showed no symptoms and the remaining 50% developed minor symptoms as opposed to PBS- or LL vector-treated mice, who all developed severe arthritis by day 24 post-CII challenge. Notably, the severity of disease symptoms was significantly less (p<0.001) in the LL-IL35-treated mice exhibiting an average clinical score of 1 in contrast to PBS- or LL vector-treated mice eventually achieving clinical scores of ~9 (FIG. 11B). To test if LL-IL35 is effective in arresting the disease after disease onset, additional groups of CIA mice were treated using a two-dose regimen on days 18 and 25. Under this treatment, 40% of the LL-IL35-treated mice developed CIA versus 100% of those treated with PBS or LL vector (FIG. 1C). Compared to the three-dose regimen, the disease severity was greater for the LL-IL35-treated CIA mice subjected to the two-dose regimen, although significantly less (p<0.05) when compared to similarly treated PBS- or LL vector-dosed mice. These data show that LL-IL35 can effectively reduce the symptoms of arthritis and the incidence of disease via its immunosuppressive capacity. Moreover, these results show that fewer doses of IL-35 delivered by LL are needed to curtail arthritis when compared to treatment with soluble protein (Niedbala et al., *Eur J Immunol.* 37(11):3021-9, 2007; Kochetkova et al., *J Immunol.* 184(12):7144-53, 2010; Singh et al., *Sci Rep.* 5:12633, 2015; Wang et al., *J Cell Mol Med.* 22(2):1014-1025, 2018).

Figures 2A, 2B:
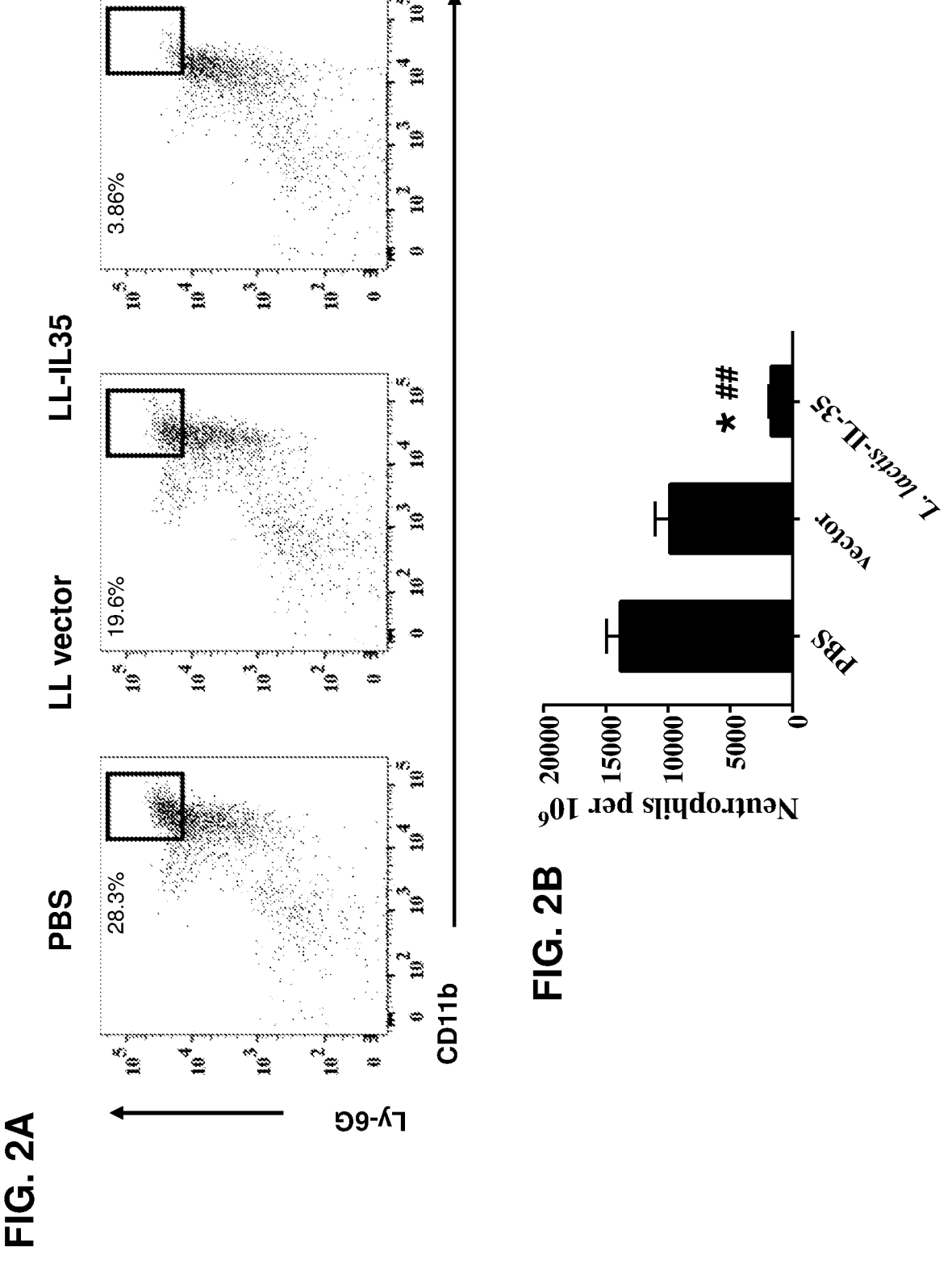
FIGS. 2A-2B. Oral LL-IL35 confers protection against CIA via reduction of neutrophil influx into joints. Reduced clinical scores and disease incidence described in FIG. 1B are attributed to reduced neutrophil infiltration into the joints of LL-IL35-treated mice when compared to PBS-dosed and LL vector-treated mice.

Analysis of knee joints was performed to determine the extent of neutrophil infiltration. In agreement with these clinical findings, the LL-IL35-treated mice had markedly reduced Ly-6G$^+$ CD11 b$^+$ cells (neutrophils) infiltrating the joints (FIG. 2A) representing a 7- and 5-fold reduction compared to PBS-dosed or LL vector-treated groups, respectively (FIG. 2B). Hence, IL-35 can reduce inflammation of the joints in CIA-challenged mice.

Figure 3C:
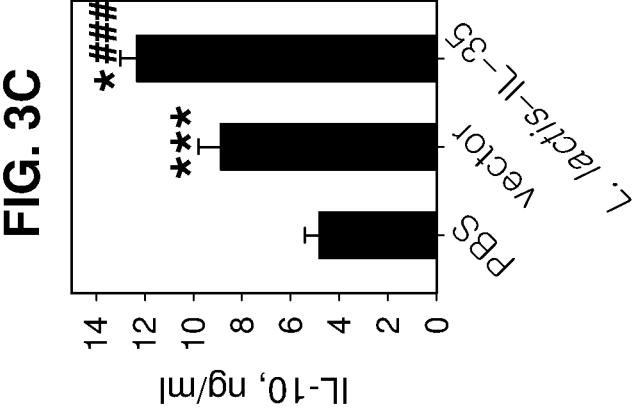
FIGS. 3A-3C. LL-IL35 reduces proinflammatory cytokines, IFN-γ and IL-17, with a concomitant increase in anti-inflammatory IL-10 production. CD4+ T cells were purified from PBS- or LL-IL35-dosed mice that received three treatments as described in FIG. 1B. The LN CD4+ T cells were stimulated with plate-bound anti-CD3 and soluble anti-CD28 for 48-72 hours, and collected supernatants were analyzed for (FIG. 3A) IFN-γ, (FIG. 3B) IL-17, and (FIG. 3C) IL-10 production. Depicted are the means±SD of triplicate cultures as assessed by cytokine-specific ELISA; *p<0.001, ***p<0.05 versus PBS-dosed mice; #p<0.001, ###p<0.01, ####p<0.05 versus LL vector-treated mice.
Figure 3B:
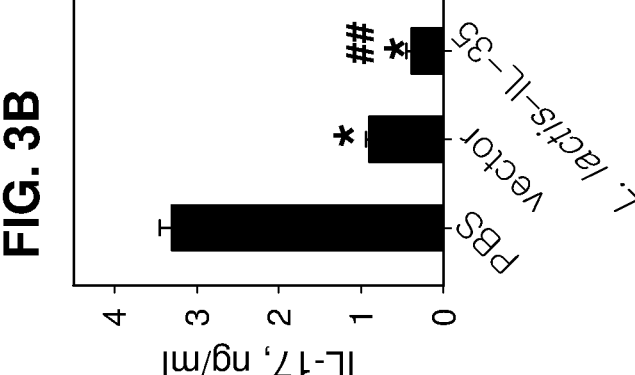
Figure 3A:
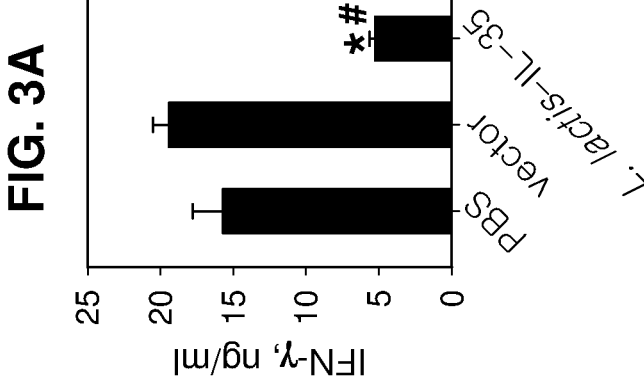

To investigate the possible mechanism of protection conferred by LL-IL35, CD4$^+$ T cells purified from draining LNs were anti-CD3+ anti-CD28-restimulated and analyzed for cytokine production. These CD4$^+$ T cells were obtained from mice dosed three times with PBS, LL vector, or LL-IL35 as described in FIG. 1B. IFN-γ levels remained elevated between PBS-dosed and LL vector-treated mice, in contrast to LL-IL35-treated mice showing 3- to 3.7-fold reduction (p<0.001; FIG. 3A). Concomitantly, IL-17 levels were significantly less (p<0.001) by 3.7- and 8.5-fold for LL vector and LL-IL35-treated groups, respectively, relative to PBS-dosed mice (FIG. 3B). Moreover, treatment with LL-IL35 significantly reduced IL-17 by 2.3-fold compared to LL vector-treated mice (p<0.01). Minimal stimulation of IL-10 was detected in the restimulated CD4$^+$ T cells from the PBS-dosed mice (FIG. 3C). In contrast, CD4$^+$ T cells from LL vector- and LL-IL35-treated groups showed significantly increased IL-10 production (p<0.05) by 1.8- and 2.5-fold, respectively. The difference between the LL vector- and LL-IL35-treated groups was significant (p<0.05; FIG. 3C) as well. The stimulation of IL-10 by LL vectors has been reported by others (Smelt et al., *PLoS One* 7(10):e47244, 2012; Huibregtse et al., *Gastroenterology* 133(2):517-28, 2007). However, IL-10 induced by the LL vector-treated group was insufficient to suppress disease progression (FIG. 1) and IL-17 production (FIG. 3B). IL-10's importance for suppressing CIA was previously demonstrated in IL-10$^{-/-}$ mice with CIA being refractive to IL-35 treatment (Kochetkova et al., *J Immunol.* 184(12):7144-53, 2010), supporting the notion here of IL-10's relevance to CIA mice treated with LL-IL35. IL-35 has also been shown to stimulate IL-10 production (Maddaloni et al., *PLoS One.* 10(1): e0117825, 2015; Niedbala et al., *Eur J Immunol.* 37(11): 3021-9, 2007; Kochetkova et al., *J Immunol.* 184(12):7144-53, 2010; Collison et al., *Nat Immunol.* 11(12):1093-101, 2010).

CD39$^+$ CD4$^+$ T cells are the primary Tregs responsible for resolving CIA (Kochetkova et al., *J Immunol.* 184(12):7144-53, 2010; Kochetkova et al., *J. Immunol.* 187: 4654-4666, 2011; Kochetkova et al., *J Immunol.* 192(2):804-16, 2014). CD39 is an ectonucleoside triphosphate diphosphohydrolase-1 which hydrolyzes ATP into AMP, thus quenching inflammatory signaling by extracellular ATP (Borsellino et al., *Blood* 110: 1225-1232, 2007; Deaglio et al., *J. Exp. Med.* 204: 1257-1265, 2007). CD25$^+$ Tregs remained a subset of CD39$^+$ CD4$^+$ T cells, and that CD39 encompassed all of the Treg subsets (Kochetkova et al., *J. Immunol.* 187: 4654-4666, 2011). In fact, CD39$^+$ Tregs were protective against CIA (Maddaloni et al., *PLoS One.* 10(1):e0117825, 2015; Kochetkova et al., *J. Immunol.* 187: 4654-4666, 2011). These Tregs are composed of two subsets, Foxp3$^+$ and Foxp3$^-$, and are interchangeable (Kochetkova et al., *J. Immunol.* 187: 4654-4666, 2011). Analysis of induction of CD39$^+$ Tregs by the LL vector revealed no increase in the percentage of these Tregs in CIA mice (Maddaloni et al., *PLoS One.* 10(1):e0117825, 2015), and CIA had only a modest impact upon their induction (Maddaloni et al., *PLoS One.* 10(1):e0117825, 2015; Kochetkova et al., *J Immunol.* 192(2):804-16, 2014).

Figure 4A:
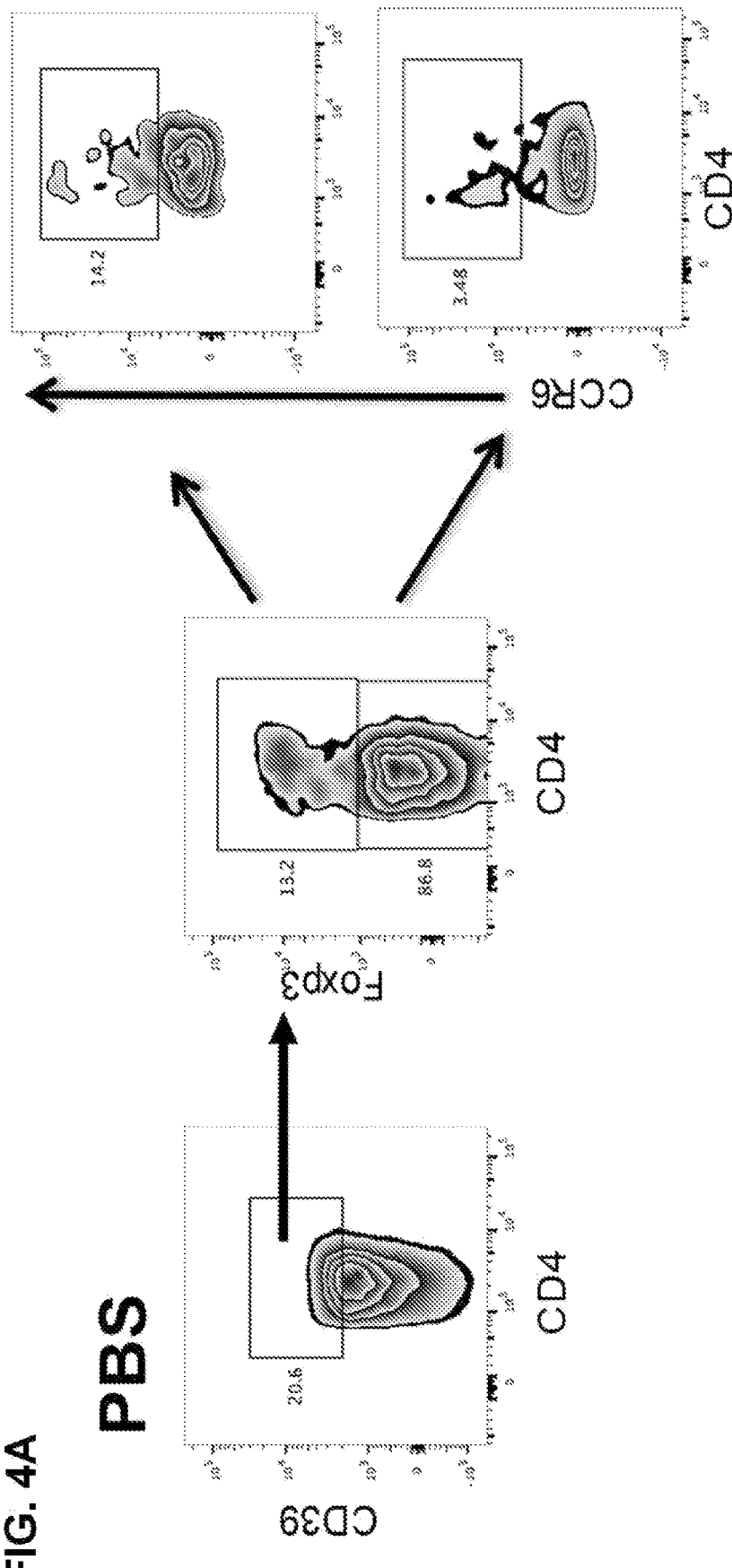
FIGS. 4A-4R. LL-IL35 induces CCR6+ and CCR6- CD39+ CD4+ T cells in CIA mice. At the termination of the study, whole splenic and LN lymphocytes were restimulated with 50 μg/ml CII overnight, and then subjected to a short-term of PMA+ ionomycin. LN CD39+ CD4+ T cells from (FIG. 4A) PBS-dosed and (FIG. 4B) LL-IL35-treated mice were gated on Foxp3+ and Foxp3- cells, and analyzed for (FIG. 4C-4R) for CCR6 expression by (FIGS. 4C, 4E, 4G, 4I, 4K, 4M, 4O, 4Q) splenic and (FIGS. 4D, 4F, 4H, 4J, 4L, 4N, 4P, 4R) LN lymphocytes.
Figure 4B:
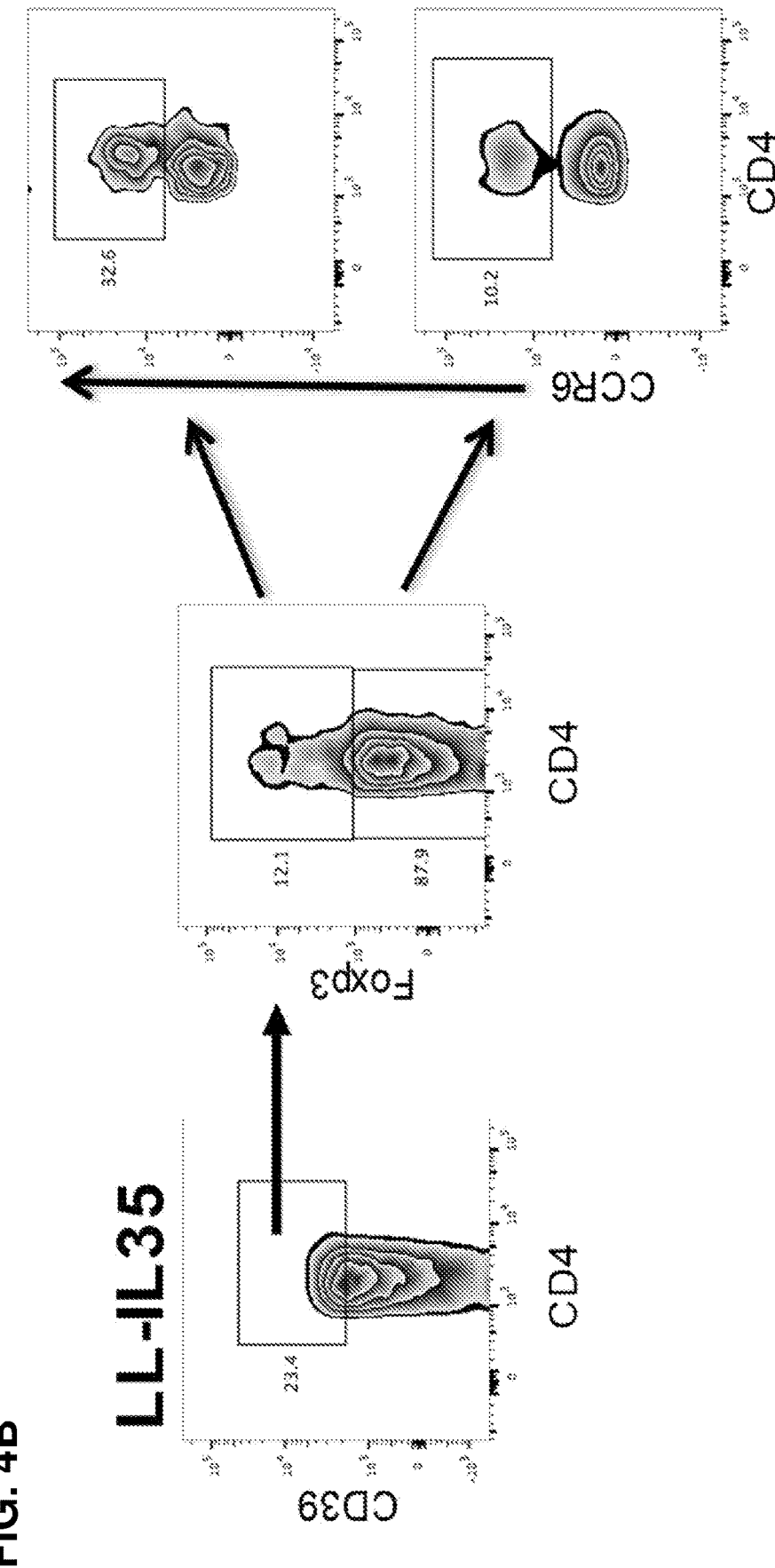
(FIGS. 4C, 4D) Frequency of CCR6$^+$ Foxp3$^+$ and (FIGS. 4E, 4F) CCR6$^+$ Foxp3$^-$ and absolute (FIGS. 4G, 4H) CCR6$^+$ Foxp3$^+$ and (FIGS. 4I, 4J) CCR6$^+$ Foxp3$^-$ T cells are shown.
(FIGS. 4K, 4L) Frequency of CCR6$^-$ Foxp3$^+$ and (FIGS. 4M, 4N) CCR6$^-$ Foxp3$^-$ and absolute (FIGS. 4O, 4P) CCR6$^-$ Foxp3$^+$ and (FIGS. 4Q, 4R) CCR6$^-$ Foxp3$^-$ T cells are also shown. Depicted are the means±SEM of 5 mice/group; *p<0.001, p≤0.010, and *p<0.05 compared with PBS-dosed mice. Scale in FIGS. 4A and 4B is log, 0 to $10^5$ on the X-axis for each plot; it is $-10^3$ or $-10^4$ to $10^5$ on the Y-axis for each plot.

To examine the types of Tregs induced by LL-IL35 treatment, whole splenic and draining LN lymphocytes were cultured overnight with CII, and then pulsed with PMA+ ionomycin to ascertain the type of Tregs induced in PBS-dosed and LL-IL35-treated mice. Lymphocytes were then stained for CD39, Foxp3, and CCR6 to identify the Treg subsets. Since CCR6 has been shown to be expressed by Tregs (Kleinewietfeld et al., *Blood* 105(7):2877-86, 2005; Rivino et al., *J Exp Med.* 207(3):565-77, 2010; Li et al., *Int J Clin Exp Med.* 8(9):15043-53, 2015), it was hypothesized that such Tregs may be induced as a consequence of IL-35 treatment. CD39$^+$ CD4$^+$ T cells were evaluated for expression of Foxp3 and CCR6 (FIGS. 4A, 4B). Upon examination of splenic Tregs derived from PBS-dosed mice compared to those present in LL-IL35-treated mice, a modest increase (p<0.05) in the frequency, but not the total number of CCR6$^+$ Foxp3$^+$ CD39$^+$ CD4$^+$ T cells, was observed (FIGS. 4C, 4G). A modest difference (p≤0.01) was also observed in the frequency and total number of splenic CCR6$^+$ Foxp3$^-$ CD39$^+$ CD4$^+$ T cells when compared to the PBS-dosed mice (FIGS. 4E, 4I). However, when similar analysis was performed for Tregs obtained from the draining LNs, a 2.2-fold increase in the frequency (p<0.001) of CCR6$^+$ Foxp3$^+$ CD39$^+$ CD4$^+$ T cells was stimulated by LL-IL35 treatment compared to those present in PBS-dosed CIA mice (FIG. 4D). The total number of these LN Tregs was also significantly (p≤0.01) increased by 2.7-fold (FIG. 4H). Subsequent analysis was performed on LN CCR6$^+$ Foxp3$^-$ CD39$^+$ CD4$^+$ T cells, and both the frequency and total number increased significantly by 2.9–(p≤0.01) and 5.1-fold (p<0.001), respectively (FIGS. 4F, 4J). These studies demonstrate that indeed CCR6$^+$ Tregs are induced by IL-35 treatment of CIA mice.

Additional analyses were performed on both CCR6$^-$ Foxp3$^+$ and CCR6$^-$ Foxp3$^-$ CD39$^+$ CD4$^+$ T cells (FIGS. 4K-4R). Examination of the splenic CCR6$^-$ Foxp3$^+$ CD39$^+$ CD4$^+$ T cells revealed that both the frequency and total number were modestly and significantly (p<0.05) reduced for the LL-IL35-treated mice (FIGS. 4K, 4O). The frequency of splenic CCR6$^-$ Foxp3$^-$ CD39$^+$ CD4$^+$ T cells was slightly and significantly (p≤0.01) reduced (FIG. 4M), but the total number of these CD39$^+$ CD4$^+$ T cells showed no difference between PBS-dosed and LL-IL35-treated CIA mice (FIG. 4Q). Similar analysis was also performed for the LN CCR6$^-$ Foxp3$^+$ and CCR6$^-$ Foxp3$^-$ CD39$^+$ CD4$^+$ T cells from the same treated CIA mice. While a slight reduction in the frequency of LN CCR6$^-$ Foxp3$^+$ CD39$^+$ CD4$^+$ T cells was observed for LL-IL35-treated mice (FIG. 4L), the total number of CCR6$^-$ Tregs was significantly (p≤0.01) elevated by 5-fold (FIG. 4P). Examination of the frequency of LN CCR6$^-$ Foxp3$^-$ CD39$^+$ CD4$^+$ T cells also showed a modest, but significant (p<0.001) reduction in LL-IL35-treated mice relative to PBS-dosed mice (FIG. 4N), but the total number of these LN T cells was significantly (p<0.001) enhanced by 36% (FIG. 4R). Hence, these analyses demonstrate that IL-35 treatment stimulates diverse subsets of Tregs including both CCR6$^+$ and CCR6$^-$ Tregs. Future studies will need to consider the longevity of these subsets for protection against CIA.

Figure 5B:
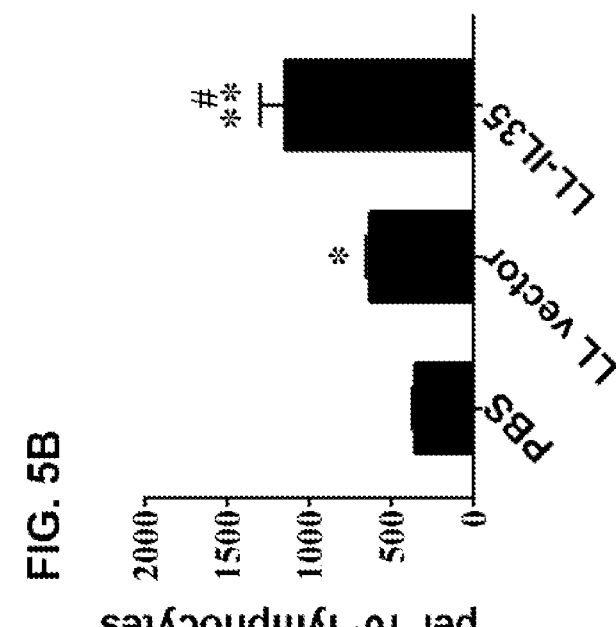
FIGS. 5A-5B. LL-IL35 stimulates IL-10 production by CD39$^+$ Tregs and CCR6$^+$ CD39$^+$ Tregs. CIA mice treated with PBS, LL vector, or LL-IL35 as described in FIG. 4. Intracellular IL-10 was measured for (FIG. 5A) CD39$^+$ CD4$^+$ and (FIG. 5B) CCR6$^+$ CD39$^+$ CD4$^+$ T cells. Depicted are the means±SEM of 5 mice/group; *p<0.001, **p<0.01 versus PBS-dosed mice; $^#$p≤0.01 versus LL vector-treated mice.
Figure 5A:
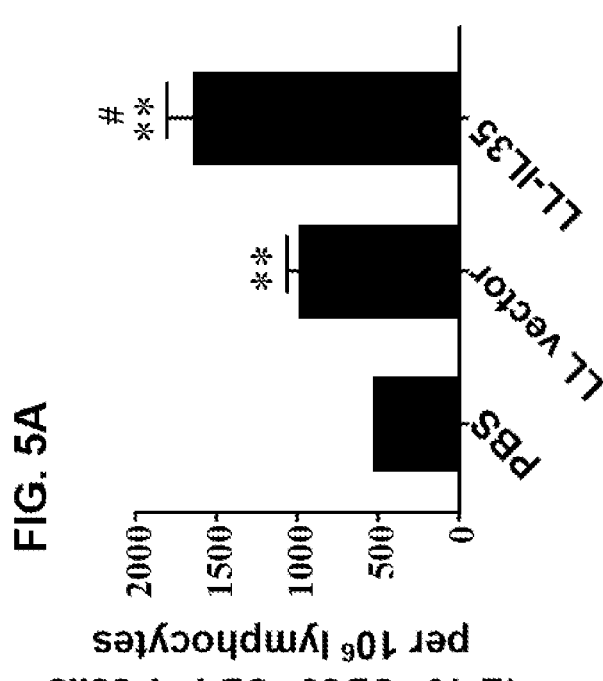
Figures 6A, 6B:
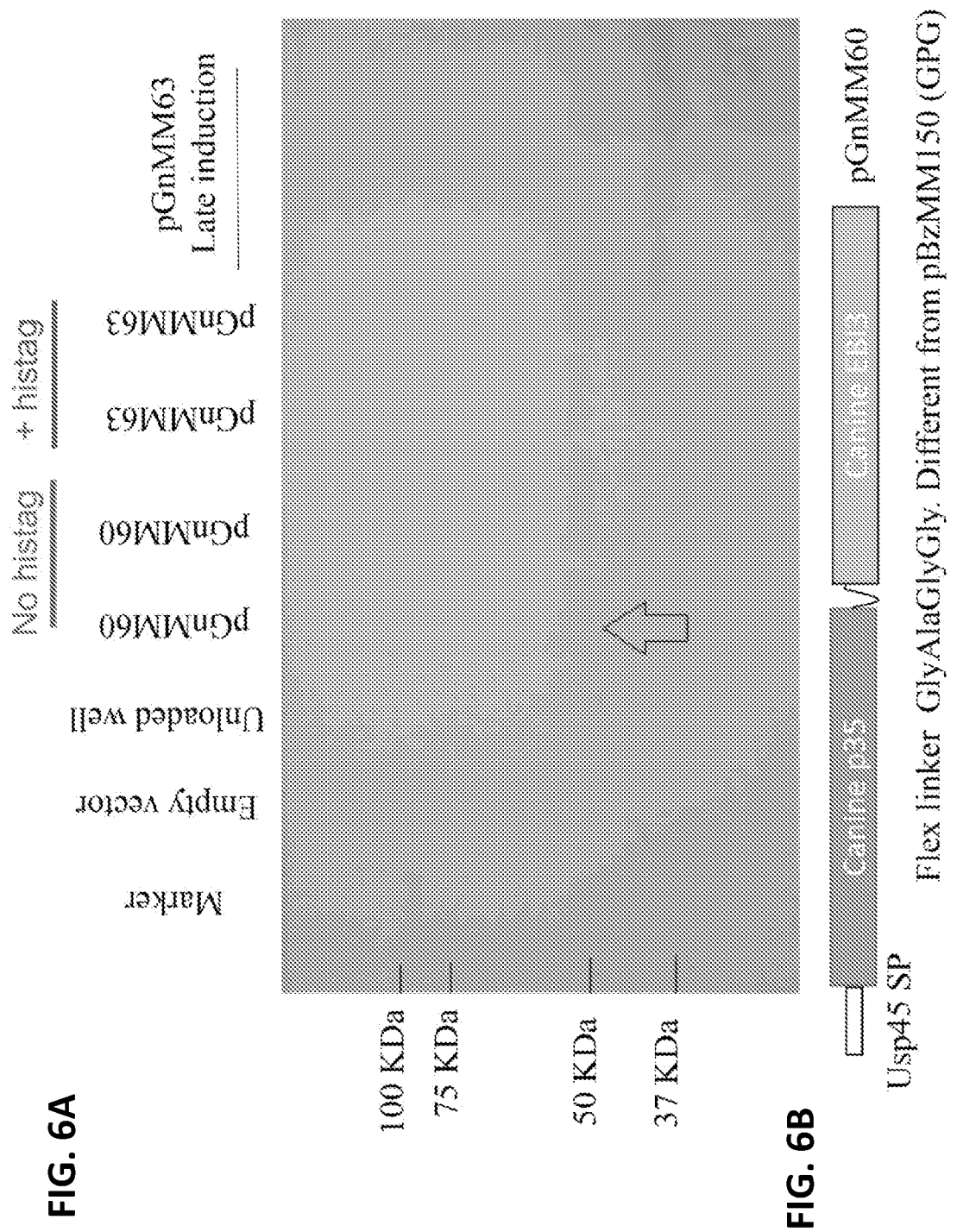
FIGS. 6A-6B illustrates Canine IL-35.

Inquiring into the activity of these LN CD39$^+$ Tregs, analysis for IL-10 production was performed (FIG. 5). Intracellular IL-10 measurements were conducted first for all CD39$^+$ CD4$^+$ T cells (both Foxp3$^+$ and Foxp3$^-$). The LL-IL35-treated mice showed 3.2- and 1.7-fold more IL-10- producing cells (p≤0.01) than PBS-dosed and LL vector-treated CIA mice, respectively (FIG. 5A). LL vector-treated mice showed 1.9-fold increase in the number of IL-10-producing CD39⁺ CD4⁺ T cells compared to PBS-dosed mice (p≤0.01; FIG. 5A). Examination of IL-10⁺ CCR6⁺ CD39⁺ CD4⁺ T cells (both Foxp3⁺ and Foxp3⁻) revealed that two-thirds of the total IL-10-producing cells induced by LL-IL35 treatment of CIA mice were derived from the CCR6⁺ subset (FIG. 5B). The CCR6⁺ CD39⁺ CD4⁺ T cells induced with LL-IL35 resulted in significant 3.2- and 1.8-fold increase in IL-10-producing cells than those present in PBS-dosed (p≤0.01) and LL vector-treated CIA mice (p<0.01), respectively. LL vector-treated mice showed 1.8-fold increase in the number of IL-10-producing CCR6⁺ CD39⁺ CD4⁺ T cells compared to PBS-dosed mice (p≤0.01; FIG. 5B). These findings suggest that indeed both Foxp3⁺ and Foxp3⁻ CCR6⁺ CD39⁺ Tregs are the predominant source of IL-10, thus contributing to the amelioration of CIA subsequent LL-IL35 treatment. Such finding may mimic what is evident with human peripheral blood CCR6⁺ CD39⁺ Tregs (Magid-Bernstein et al., *J Interferon Cytokine Res.* 37(4):153-164, 2017) and CCR6⁺ Tregs found in patients with glomerulonephritis (Kluger et al., *J Am Soc Nephrol.* 25(6):1291-302, 2014).

The data presented demonstrate the potency of IL-35 as an anti-inflammatory therapeutic. Moreover, this investigation further supports the multifaceted benefits of adapting recombinant *L. lactis* as a vector to deliver therapeutic doses of IL-35. In fact, previous studies by us (Kochetkova et al., *J Immunol.* 184(12):7144-53, 2010) or others, using IL-35 to treat type 1 diabetes model (Singh et al., *Sci Rep.* 5:12633, 2015), IBD (Wang et al., *J Cell Mol Med.* 22(2):1014-1025, 2018), or psoriasis (Wang et al., *J Cell Mol Med.* 22(2): 1014-1025, 2018), required daily treatments with recombinant protein to control disease. In contrast, only two or three oral doses of LL-IL35 were sufficient to prevent the onset or stop CIA progression. Oral dosing has the substantial advantage of being less invasive circumventing the need for injections. LL-derived IL-35 eliminates the labor-intensive efforts needed to produce and purify the recombinant protein, dramatically reducing the cost of manufacturing this therapeutic. Moreover, IL-35 is a dimeric protein which adds to the difficulty and cost to generate. The *L. lactis* used for this study is a lab-adapted recombinant, originally derived from an industrial dairy strain capable of fermenting milk into a product that has the same textural and olfactory properties of yogurt. It has been demonstrated that the curative properties of recombinant *L. lactis* are maintained when grown on a synthetic medium or used to ferment milk into a yogurt-like product (Maddaloni et al., *PLoS One.* 10(1):e0117825, 2015). These attributes make *L. lactis* an ideal tolerogen delivery platform for the treatment of auto-immune diseases.

Example 2: Production and Testing of a Murine IL-35 Fusion Protein Having Murine EBI3 Upstream to p35, with a Rigid Linker Using methods similar to those described in Example 1, another murine IL-35 fusion protein expression construct was constructed, in which the IL-35 subunits were in the reverse order—that is, EBI3/IL-27β followed by p35/IL-12α (see FIG. 7A). This fusion was expressed in pGnMM121 and produced substantially more protein than the other subunit order (p35/IL-12α followed by EBI3/IL-27β, exemplified by SEQ ID NO: 2 (murine), SEQ ID NO: 5 (canine), and SEQ ID NO: 7 (human)).

The expression cassette sequence borne on pGnMM119 (shown in SEQ ID NOs: 10 & 11) and pGnMM121 (used in the current example) is identical. The difference is the backbone: pGnMM119 is the pUC-based construct/cloning vector bearing the synthetic gene (as it was provided by GenScript). The pGnMM121 bears the same sequence after AgeI cloning (ACCGGT) into the pMSP3535H3 vector, which is the shuttle vector that was used for expression in *Lactococcus*.

Figures 7A, 7B:
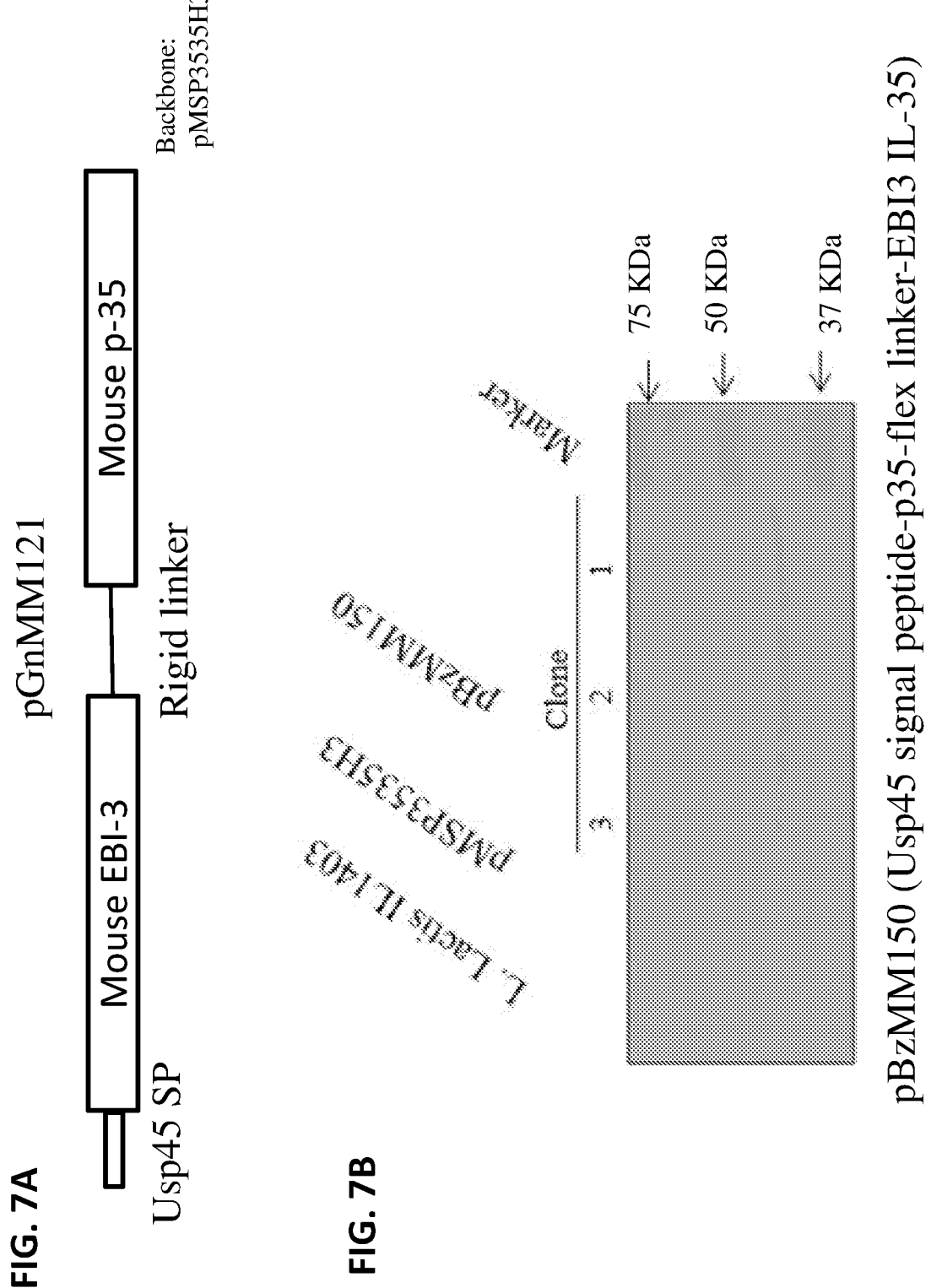
FIGS. 7A-7C illustrate a second Murine IL35, in which the EBI3 and p35 subunits are in the reversed order compared to, for instance, the fusion illustrated in FIG. 6B.

FIG. 7B shows the results of induced expression of pBzMM150. The configuration of the synthetic gene in this construct is Usp45 signal peptide—p35—short flexible linker—EBI3. The expression is driven by the Nisin-inducible promoter.

Figure 7C:
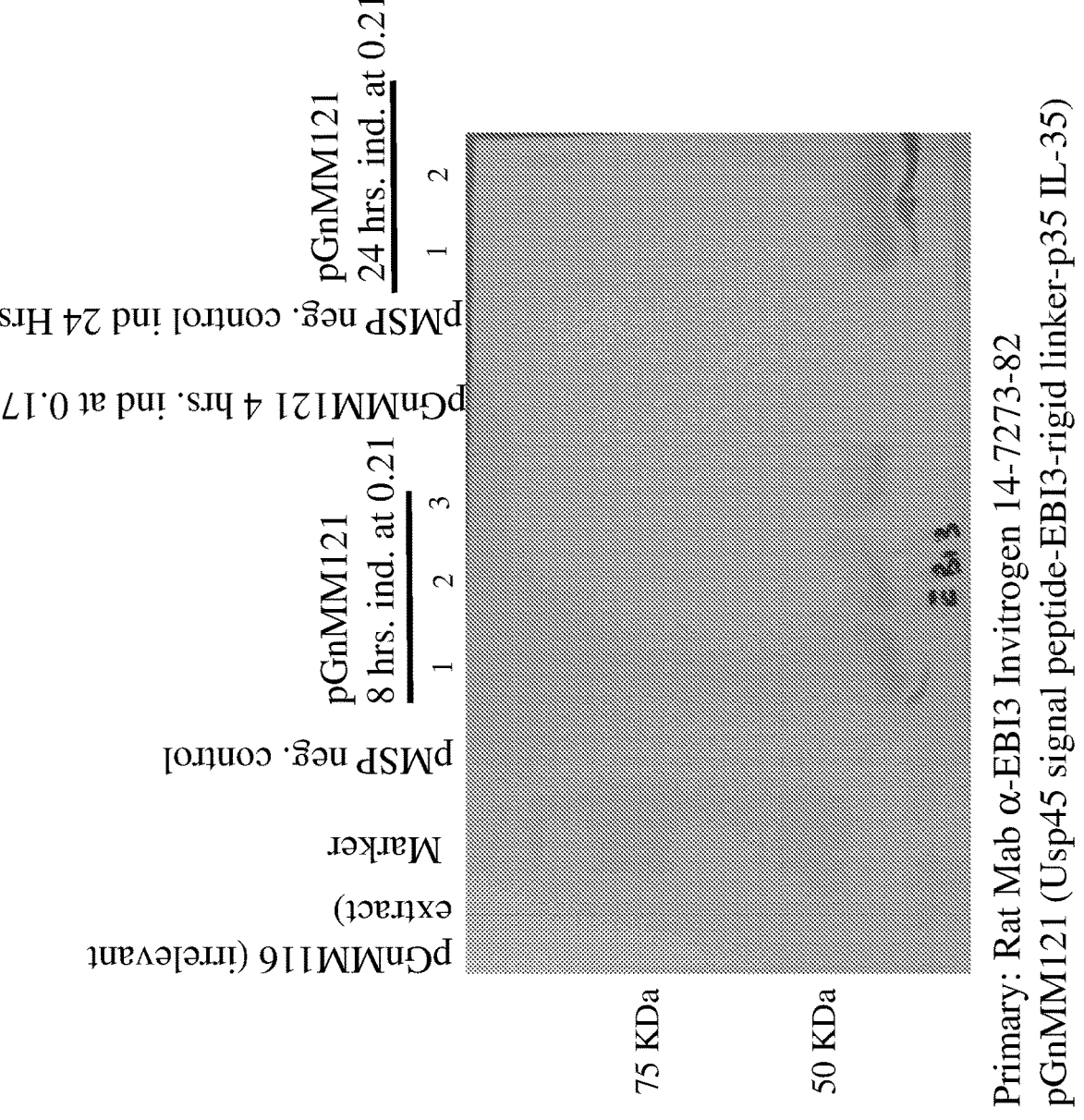

FIG. 7C shows the results of induced expression of pGnMM121. The configuration of the synthetic gene in this construct is Usp45 signal peptide-EBI3-long rigid linker-p35. The expression is driven by the Nisin-inducible promoter. (Expression using a constitutive promoter is detrimental to high expression.) It is clear, comparing FIG. 7B to 7C, that the level of protein production from pGnMM121 is higher than that from pBzMM150.

In both cases (pBzMM150 and pGnMM121), IL-35 migrates slightly lower than expected. This may be an artifact caused by the folding properties of p35.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect, in this context, is a measurable alteration in the biological function of a described engineered, single-chain mammalian IL-35, a bacterial cell expressing that protein, or a composition containing the protein and/or a bacterial cell expressing it.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A composition, comprising:
   a recombinant lactic acid bacterial cell, comprising:
   a nucleotide sequence encoding an engineered, single-chain mammalian IL-35, wherein the recombinant lactic acid bacterial cell expresses an engineered, single-chain mammalian IL-35 protein comprising the amino acid sequence shown in SEQ ID NO: 7 (human), SEQ ID NO: 2 (murine), SEQ ID NO: 11 (murine), or SEQ ID NO: 5 (canine) from the engineered, single-chain mammalian IL-35 nucleotide sequence.

2. The composition of claim 1, formulated for treatment of an autoimmune or inflammatory disease.

3. The composition of claim 1, wherein the nucleotide sequence encoding the engineered, single-chain mammalian IL-35 is integrated into the genome of the recombinant lactic acid bacterial cell.

4. The composition of claim 1, which is formulated as a milk-based nutraceutical.

5. The composition of claim 4, wherein the milk-based nutraceutical is a fermented milk product.

6. The composition of claim 5, wherein the fermented milk product comprises a yogurt, a buttermilk, a kefir, a cheese, a crème fraiche, or a cultured sour cream.

7. A recombinant lactic acid bacterial cell, comprising:
   a nucleotide sequence encoding an engineered, single-chain mammalian IL-35, wherein the recombinant lactic acid bacterial cell expresses SEQ ID NO: 7 (human), SEQ ID NO: 2 (murine), SEQ ID NO: 11 (murine), or SEQ ID NO: 5 (canine) from an engineered, single-chain mammalian IL-35 nucleotide sequence.

8. The recombinant lactic acid bacterial cell of claim 7, wherein the nucleotide sequence encoding the engineered, single-chain mammalian IL-35 comprises the sequence of positions 31-1395 of SEQ ID NO: 6, positions 31-1371 of SEQ ID NO: 1, positions 25-1332 of SEQ ID NO: 10, or positions 25-1332 of SEQ ID NO: 4.

9. The recombinant lactic acid bacterial cell of claim 7, wherein the recombinant lactic acid bacterial cell is a cell from the genus Lactococcus.

10. The recombinant lactic acid bacterial cell of claim 7, wherein the nucleotide sequence encoding the engineered, single-chain mammalian IL-35 is integrated into the genome of the recombinant lactic acid bacterial cell.

11. A method for treating or preventing an autoimmune or inflammatory disease in a subject, comprising:
    administering to the subject the composition of claim 1.

12. The method of claim 11, wherein:
    the level of IL-10 in the subject is increased upon the administering, as compared to the level of the IL-10 present in the subject before the administering; and/or
    the level of TGF-β in the subject is increased upon the administering, as compared to the level of the TGF-β present in the subject before the administering; and/or
    the level of at least one of IFN-γ or IL-17 is decreased upon the administering, as compared to the level of at least one of IFN-γ or IL-17 present in the subject before the administering; and/or
    the level of TNF-α is decreased upon the administering, as compared to the level of TNF-α present in the subject before the administering.

13. A method for producing a composition for treatment of an autoimmune or inflammatory disease, comprising:
    introducing a nucleotide sequence encoding an engineered, single-chain mammalian IL-35 into a recipient lactic acid bacterial cell to produce a recombinant lactic acid bacterial cell, wherein the recombinant lactic acid bacterial cell expresses SEQ ID NO: 7 (human), SEQ ID NO: 2 (murine), SEQ ID NO: 11 (murine), or SEQ ID NO: 5 (canine) from an engineered, single-chain mammalian IL-35 nucleotide sequence.

14. The method of claim 13, wherein the nucleotide sequence comprises the sequence of positions 31-1395 of SEQ ID NO: 6, positions 31-1371 of SEQ ID NO: 1, positions 25-1332 of SEQ ID NO: 10, or positions 25-1332 of SEQ ID NO: 4.

15. The method of claim 14, wherein nucleotide sequence comprises the sequence of SEQ ID NO: 6 (human), SEQ ID NO: 1 (murine), SEQ ID NO: 10, or SEQ ID NO: 4 (canine).

16. The method of claim 13, further comprising:
    culturing the lactic acid bacterial cell under conditions which allow for expression of the engineered, single-chain mammalian IL-35.

17. The method of claim 13, wherein introducing the nucleotide sequence encoding the engineered, single-chain mammalian IL-35 comprises integrating the encoding sequence into the genome of the recipient lactic acid bacterial cell.

* * * * *

SEQUENCE LISTING

```
<160> NUMBER OF SEQ ID NOS: 11

<210> SEQ ID NO 1
<211> LENGTH: 1377
<212> TYPE: DNA
<213> ORGANISM: Artificial Sequence
<220> FEATURE:
<223> OTHER INFORMATION: Synthetic construct, based on murine IL-35;
      details provided in specification

<400> SEQUENCE: 1
accggtcccg ggtaccagga ggtcgacgat atgaaaaaga aaattatctc agctatttta      60
atgtctacag tgatactttc tgctgcagcc ccgttgtcag gtgtttacgc tgatactaac     120
gctagcggac gtgtaattcc agtttctggt cctgctagat gtttatcaca atctcgtaat     180
ttgcttaaaa ctacagatga catggttaag actgctagag aaaaattgaa acactattcc     240
```

```
tgtacagctg aagatattga tcatgaagac attaccagag atcaaacttc tacattgaaa      300
acatgtttac cactggaatt gcataagaat gagagttgct tagctactag agaaacatct      360
tcaactaccc gtggtagttg tttacctcca caaaaaactt ctttgatgat gactctttgt      420
ctaggttcaa tttatgaaga tcttaagatg taccaaacag agtttcaagc tatcaatgct      480
gcattgcaaa atcacaacca tcaacagatc attctagata aaggaatgtt agttgctatt      540
gatgaattga tgcaatctct taatcataat ggcgagactt tacgtcaaaa accacctgtt      600
ggagaagcag atccttatag agttaagatg aaactttgta ttctcttaca tgctttttca      660
acaagggttg taactatcaa tagagtgatg ggatatttga gttctgcagg tcctggcaat      720
ggatcaccag gtcaagggac tgatgctagc gctttagtcg ccttgtctca accacgtgtt      780
caatgtcatg cttctagata tccagtagca gttgattgct catggactcc attgcaagct      840
cctaactcta cccgtagtac ttcatttatt gccacatacc gcttaggtgt tgcaactcaa      900
cagcaatctc agccatgttt gcaacgtagc cctcaagctt cgagatgtac aattccagat      960
gtacacttgt ctctacagt gccatatatg ctaaatgtta ctgcagtaca tccaggtgga     1020
gctagttcat ctttgttagc ctttgtagct gaacgtatta tcaagccaga tcctccagaa     1080
ggagttagac ttcgaacagc tggtcagcgt ttacaagtat tgtggcatcc acctgcttct     1140
tggccgtttc cagatatttt cagtttgaaa tatcgtctga gataccgtcg acgcggagca     1200
tctcattttc gtcaagttgg tccaattgaa gctacaactt cacattgcg taatagtaaa      1260 ccacacgcaa agtattgtat tcaagtatca gctcaagatc ttacagatta tggtaaacca     1320
tctgattggt cattgcctgg gcaagtagaa agtgcaccac ataagccctg aaccggt        1377
```

<210> SEQ ID NO 2
<211> LENGTH: 446
<212> TYPE: PRT
<213> ORGANISM: Artificial Sequence
<220> FEATURE:
<223> OTHER INFORMATION: Synthetic construct, based on murine IL-35;
      details provided in specification.  Encoded by SEQ ID NO: 1.

<400> SEQUENCE: 2

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ala Ser
            20                  25                  30

Gly Arg Val Ile Pro Val Ser Gly Pro Ala Arg Cys Leu Ser Gln Ser
        35                  40                  45

Arg Asn Leu Leu Lys Thr Thr Asp Asp Met Val Lys Thr Ala Arg Glu
    50                  55                  60

Lys Leu Lys His Tyr Ser Cys Thr Ala Glu Asp Ile Asp His Glu Asp
65                  70                  75                  80

Ile Thr Arg Asp Gln Thr Ser Thr Leu Lys Thr Cys Leu Pro Leu Glu
                85                  90                  95

Leu His Lys Asn Glu Ser Cys Leu Ala Thr Arg Glu Thr Ser Ser Thr
            100                 105                 110

Thr Arg Gly Ser Cys Leu Pro Pro Gln Lys Thr Ser Leu Met Met Thr
        115                 120                 125

Leu Cys Leu Gly Ser Ile Tyr Glu Asp Leu Lys Met Tyr Gln Thr Glu
    130                 135                 140

Phe Gln Ala Ile Asn Ala Ala Leu Gln Asn His Asn His Gln Gln Ile
145                 150                 155                 160
```

```
Ile Leu Asp Lys Gly Met Leu Val Ala Ile Asp Glu Leu Met Gln Ser
            165                 170                 175

Leu Asn His Asn Gly Glu Thr Leu Arg Gln Lys Pro Pro Val Gly Glu
            180                 185                 190

Ala Asp Pro Tyr Arg Val Lys Met Lys Leu Cys Ile Leu Leu His Ala
            195                 200                 205

Phe Ser Thr Arg Val Val Thr Ile Asn Arg Val Met Gly Tyr Leu Ser
    210                 215                 220

Ser Ala Gly Pro Gly Asn Gly Ser Pro Gly Gln Gly Thr Asp Ala Ser
225                 230                 235                 240

Ala Leu Val Ala Leu Ser Gln Pro Arg Val Gln Cys His Ala Ser Arg
            245                 250                 255

Tyr Pro Val Ala Val Asp Cys Ser Trp Thr Pro Leu Gln Ala Pro Asn
            260                 265                 270

Ser Thr Arg Ser Thr Ser Phe Ile Ala Thr Tyr Arg Leu Gly Val Ala
            275                 280                 285

Thr Gln Gln Gln Ser Gln Pro Cys Leu Gln Arg Ser Pro Gln Ala Ser
    290                 295                 300

Arg Cys Thr Ile Pro Asp Val His Leu Phe Ser Thr Val Pro Tyr Met
305                 310                 315                 320

Leu Asn Val Thr Ala Val His Pro Gly Gly Ala Ser Ser Ser Leu Leu
            325                 330                 335

Ala Phe Val Ala Glu Arg Ile Ile Lys Pro Asp Pro Pro Glu Gly Val
            340                 345                 350

Arg Leu Arg Thr Ala Gly Gln Arg Leu Gln Val Leu Trp His Pro Pro
            355                 360                 365

Ala Ser Trp Pro Phe Pro Asp Ile Phe Ser Leu Lys Tyr Arg Leu Arg
    370                 375                 380

Tyr Arg Arg Arg Gly Ala Ser His Phe Arg Gln Val Gly Pro Ile Glu
385                 390                 395                 400

Ala Thr Thr Phe Thr Leu Arg Asn Ser Lys Pro His Ala Lys Tyr Cys
            405                 410                 415

Ile Gln Val Ser Ala Gln Asp Leu Thr Asp Tyr Gly Lys Pro Ser Asp
            420                 425                 430

Trp Ser Leu Pro Gly Gln Val Glu Ser Ala Pro His Lys Pro
            435                 440                 445

<210> SEQ ID NO 3
<211> LENGTH: 204
<212> TYPE: DNA
<213> ORGANISM: Artificial Sequence
<220> FEATURE:
<223> OTHER INFORMATION: Synthetic construct, nisin-inducible promoter

<400> SEQUENCE: 3
agtcttataa ctatactgac aatagaaaca ttaacaaatc taaaacagtc ttaattctat      60
cttgagaaag tattggtaat aatattattg tcgataacgc gagcataata aacggctctg     120
attaaattct gaagtttgtt agatacaatg atttcgttcg aaggaactac aaaataaatt     180
attctagacc aggtcgcgac cggt                                           204

<210> SEQ ID NO 4
<211> LENGTH: 1344
<212> TYPE: DNA
<213> ORGANISM: Artificial Sequence
<220> FEATURE:
```

-continued

<223> OTHER INFORMATION: Synthetic construct, based on canine IL-35;
      details provided in specification

<400> SEQUENCE: 4

```
accggttaca aggaggttga caatatgaaa aagaaaatta tctcagctat tctgatgtct      60
acagtgatac tttctgctgc agccccgttg tcaggtgttt acgctgatac taacgctagc     120
agatctttac caacagcttc accatctcct ggaatctttc aatgtttgaa tcattctcaa     180
aacttgttac gtgctgtaag caatacactt caaaaagcta gacaaacttt ggattacatt     240
ccatgtacat ctgaagagat tgatcatgaa gacattacaa aagataaaac ttcaacagtt     300
gaagcatgct taccattgga acttactatg aatgaaagtt gcttagcttc acgtgaaatc     360
tctttgatta ctaatggaag ttgtttagca tctggtaaag ctagctttat gacagtgtta     420
tgtcttagtt caatctatga agatttgaaa atgtatcaaa tggaattcaa agctatgaat     480
gcaaagttgt aatggatcc aaaacgtcaa atctttcttg atcaaaacat gttgacagct     540
atcgatgaat tgttacaagc attgaatttc aatagtgtga ctgttccaca gaaatctagt     600
cttgaagagc cagatttcta taagactaaa atcaagttat gtattctttt gcatgctttt     660
cgtattagag cagttactat cgatcgtatg atgagttact tgaattcttc aggtgcagga     720
ggtccaactc aacctcgtgt aagatgtcgt gcatctcgat atccagttgc tgtggattgt     780
ttttggacat tgccacctgc tccacgttca gcaactccta catcttttat cgccacatat     840
cgtcttggag tagctgcaca tggtgaatca ttaccatgtt tgcaacagac acctgaagct     900
acttcatgta caattccaga tgtgcatatg ttttcaatgg taccttacgt attgaatgtt     960
acagcagtac gtccatgggg aagttcatct agctttgtac catttgttcc agaacaattg    1020
attaaacctg atcctccaga aggtgtacgt ttaagtgttc ttccaagaca acgtttgtgg    1080
gtacaatggg aacctccacg ttcatggcct tttccagaat tgtttagtct gaaatattgg    1140
attcgttaca acatcacgg atctccaaga tttcgtcaag taggtcctat tgaagctaca    1200
tcatttacat tcagagcagt gcgtccacaa gctcgatatt gtattcaagt agcagctcaa    1260
gatttgacag attatggaga atcaagtgat tggtctttgc ctgctgcacc ttctacacca    1320
cttggcaaat agcccgggac cggt                                          1344
```

<210> SEQ ID NO 5
<211> LENGTH: 435
<212> TYPE: PRT
<213> ORGANISM: Artificial Sequence
<220> FEATURE:
<223> OTHER INFORMATION: Synthetic construct, based on canine IL-35;
      details provided in specification.  Encoded by SEQ ID NO: 4.

<400> SEQUENCE: 5

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ala Ser
            20                  25                  30

Arg Ser Leu Pro Thr Ala Ser Pro Ser Pro Gly Ile Phe Gln Cys Leu
        35                  40                  45

Asn His Ser Gln Asn Leu Leu Arg Ala Val Ser Asn Thr Leu Gln Lys
    50                  55                  60

Ala Arg Gln Thr Leu Asp Tyr Ile Pro Cys Thr Ser Glu Glu Ile Asp
65                  70                  75                  80

His Glu Asp Ile Thr Lys Asp Lys Thr Ser Thr Val Glu Ala Cys Leu
                85                  90                  95
```

-continued

```
Pro Leu Glu Leu Thr Met Asn Glu Ser Cys Leu Ala Ser Arg Glu Ile
            100                 105                 110

Ser Leu Ile Thr Asn Gly Ser Cys Leu Ala Ser Gly Lys Ala Ser Phe
            115                 120                 125

Met Thr Val Leu Cys Leu Ser Ser Ile Tyr Glu Asp Leu Lys Met Tyr
            130                 135                 140

Gln Met Glu Phe Lys Ala Met Asn Ala Lys Leu Leu Met Asp Pro Lys
145                 150                 155                 160

Arg Gln Ile Phe Leu Asp Gln Asn Met Leu Thr Ala Ile Asp Glu Leu
                165                 170                 175

Leu Gln Ala Leu Asn Phe Asn Ser Val Thr Val Pro Gln Lys Ser Ser
            180                 185                 190

Leu Glu Glu Pro Asp Phe Tyr Lys Thr Lys Ile Lys Leu Cys Ile Leu
            195                 200                 205

Leu His Ala Phe Arg Ile Arg Ala Val Thr Ile Asp Arg Met Met Ser
            210                 215                 220

Tyr Leu Asn Ser Ser Gly Ala Gly Gly Pro Thr Gln Pro Arg Val Arg
225                 230                 235                 240

Cys Arg Ala Ser Arg Tyr Pro Val Ala Val Asp Cys Phe Trp Thr Leu
                245                 250                 255

Pro Pro Ala Pro Arg Ser Ala Thr Pro Thr Ser Phe Ile Ala Thr Tyr
                260                 265                 270

Arg Leu Gly Val Ala Ala His Gly Glu Ser Leu Pro Cys Leu Gln Gln
            275                 280                 285

Thr Pro Glu Ala Thr Ser Cys Thr Ile Pro Asp Val His Met Phe Ser
            290                 295                 300

Met Val Pro Tyr Val Leu Asn Val Thr Ala Val Arg Pro Trp Gly Ser
305                 310                 315                 320

Ser Ser Ser Phe Val Pro Phe Val Pro Glu Gln Leu Ile Lys Pro Asp
                325                 330                 335

Pro Pro Glu Gly Val Arg Leu Ser Val Leu Pro Arg Gln Arg Leu Trp
            340                 345                 350

Val Gln Trp Glu Pro Pro Arg Ser Trp Pro Phe Pro Glu Leu Phe Ser
            355                 360                 365

Leu Lys Tyr Trp Ile Arg Tyr Lys His His Gly Ser Pro Arg Phe Arg
            370                 375                 380

Gln Val Gly Pro Ile Glu Ala Thr Ser Phe Thr Phe Arg Ala Val Arg
385                 390                 395                 400

Pro Gln Ala Arg Tyr Cys Ile Gln Val Ala Ala Gln Asp Leu Thr Asp
                405                 410                 415

Tyr Gly Glu Ser Ser Asp Trp Ser Leu Pro Ala Ala Pro Ser Thr Pro
                420                 425                 430

Leu Gly Lys
        435
```

```
<210> SEQ ID NO 6
<211> LENGTH: 1407
<212> TYPE: DNA
<213> ORGANISM: Artificial Sequence
<220> FEATURE:
<223> OTHER INFORMATION: Synthetic construct, based on human IL-35;
      details provided in specification

<400> SEQUENCE: 6
cccgggaccg gttacaagga ggttgacaat atgaaaaaga aaattatctc agctattctg       60
```

```
atgtctacag tgatactttc tgctgcagcc ccgttgtcag gtgtttacgc tgatactaac        120
gctagcgcac gtaatcttcc tgttgcaaca ccagatcctg gaatgtttcc atgtttacat        180
cactcacaaa atttgttacg tgctgttagt aatatgcttc aaaaagcacg tcaaactttg        240
gaattttatc catgtacatc agaagagatt gatcacgaag atatcacaaa agataagact        300
tcaacagttg aagcttgttt accattggaa cttacgaaaa atgaaagctg tttaaattca        360
cgtgaaacat ctttcattac taatggatca tgtttagcta gtcgtaaaac atcatttatg        420
atggcattat gtttgtcttc aatctatgaa gatttgaaaa tgtatcaagt tgagtttaaa        480
acgatgaatg ctaaaattact tatggatcca aaacgtcaaa tttttcttga tcaaaatatg        540
cttgcagtta ttgatgaatt aatgcaagct ttgaacttta atagtgaaac agttccacaa        600
aaatcatctt tagaagagcc agatttctat aaaactaaga ttaaactttg tatcttattg        660 catgctttc gtattcgagc tgttacaatt gatcgtgtaa tgtcttattt gaatgctagt         720
ggtggaggcg ttcaggagg aggtggatct ggtggaggcg gtagtcgtaa aggacctcca         780
gctgcattga cattacctag agttcaatgt cgtgcttcac gttatccaat tgctgttgat        840
tgttcttgga cattacctcc agcacctaat tctacttcac cagttagttt cattgctaca        900
tatcgtttag gaatggcagc tcgtggtcat tcttggccat gtttgcaaca gactcctaca        960
tcaacttctt gtaccattac agatgttcaa ttgtttcaa tggctccata tgtttgaat        1020 gtaactgcag ttcatccttg gggatcatct agttcatttg ttccattcat tactgaacac       1080
ataatcaaac ctgatccacc tgaaggtgtt cgtttatcac cattggctga aagacaactt       1140
caggttcaat gggaaccacc tggaagttgg ccatttcctg aaatcttttc attgaaatat       1200
tggattcgtt ataaaagaca aggtgcagct cgttttcatc gtgttggacc tattgaagca       1260
acatcattta tccttcgtgc tgttagacct cgtgctcgat attacattca agtagcagct       1320
caagatttaa cagactatgg agaattgtca gattggtctc ttccagctac tgcaacaatg       1380
agtttaggta aataacccgg gaccggt                                          1407
```

<210> SEQ ID NO 7
<211> LENGTH: 454
<212> TYPE: PRT
<213> ORGANISM: Artificial Sequence
<220> FEATURE:
<223> OTHER INFORMATION: Synthetic construct, based on human IL-35;
      details provided in specification.  Encoded by SEQ ID NO: 6.

<400> SEQUENCE: 7

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ala Ser
            20                  25                  30

Ala Arg Asn Leu Pro Val Ala Thr Pro Asp Pro Gly Met Phe Pro Cys
        35                  40                  45

Leu His His Ser Gln Asn Leu Leu Arg Ala Val Ser Asn Met Leu Gln
    50                  55                  60

Lys Ala Arg Gln Thr Leu Glu Phe Tyr Pro Cys Thr Ser Glu Glu Ile
65                  70                  75                  80

Asp His Glu Asp Ile Thr Lys Asp Lys Thr Ser Thr Val Glu Ala Cys
                85                  90                  95

Leu Pro Leu Glu Leu Thr Lys Asn Glu Ser Cys Leu Asn Ser Arg Glu
            100                 105                 110
```

-continued

```
Thr Ser Phe Ile Thr Asn Gly Ser Cys Leu Ala Ser Arg Lys Thr Ser
        115                 120                 125

Phe Met Met Ala Leu Cys Leu Ser Ser Ile Tyr Glu Asp Leu Lys Met
        130                 135                 140

Tyr Gln Val Glu Phe Lys Thr Met Asn Ala Lys Leu Leu Met Asp Pro
145                 150                 155                 160

Lys Arg Gln Ile Phe Leu Asp Gln Asn Met Leu Ala Val Ile Asp Glu
                165                 170                 175

Leu Met Gln Ala Leu Asn Phe Asn Ser Glu Thr Val Pro Gln Lys Ser
                180                 185                 190

Ser Leu Glu Glu Pro Asp Phe Tyr Lys Thr Lys Ile Lys Leu Cys Ile
                195                 200                 205

Leu Leu His Ala Phe Arg Ile Arg Ala Val Thr Ile Asp Arg Val Met
        210                 215                 220

Ser Tyr Leu Asn Ala Ser Gly Gly Gly Ser Gly Gly Gly Gly Ser
225                 230                 235                 240

Gly Gly Gly Gly Ser Arg Lys Gly Pro Pro Ala Ala Leu Thr Leu Pro
                245                 250                 255

Arg Val Gln Cys Arg Ala Ser Arg Tyr Pro Ile Ala Val Asp Cys Ser
                260                 265                 270

Trp Thr Leu Pro Pro Ala Pro Asn Ser Thr Ser Pro Val Ser Phe Ile
        275                 280                 285

Ala Thr Tyr Arg Leu Gly Met Ala Ala Arg Gly His Ser Trp Pro Cys
        290                 295                 300

Leu Gln Gln Thr Pro Thr Ser Thr Ser Cys Thr Ile Thr Asp Val Gln
305                 310                 315                 320

Leu Phe Ser Met Ala Pro Tyr Val Leu Asn Val Thr Ala Val His Pro
                325                 330                 335

Trp Gly Ser Ser Ser Ser Phe Val Pro Phe Ile Thr Glu His Ile Ile
                340                 345                 350

Lys Pro Asp Pro Pro Glu Gly Val Arg Leu Ser Pro Leu Ala Glu Arg
                355                 360                 365

Gln Leu Gln Val Gln Trp Glu Pro Pro Gly Ser Trp Pro Phe Pro Glu
        370                 375                 380

Ile Phe Ser Leu Lys Tyr Trp Ile Arg Tyr Lys Arg Gln Gly Ala Ala
385                 390                 395                 400

Arg Phe His Arg Val Gly Pro Ile Glu Ala Thr Ser Phe Ile Leu Arg
                405                 410                 415

Ala Val Arg Pro Arg Ala Arg Tyr Tyr Ile Gln Val Ala Ala Gln Asp
                420                 425                 430

Leu Thr Asp Tyr Gly Glu Leu Ser Asp Trp Ser Leu Pro Ala Thr Ala
                435                 440                 445

Thr Met Ser Leu Gly Lys
        450
```

```
<210> SEQ ID NO 8
<211> LENGTH: 12
<212> TYPE: PRT
<213> ORGANISM: Artificial Sequence
<220> FEATURE:
<223> OTHER INFORMATION: Synthetic linker peptide

<400> SEQUENCE: 8

Ala Glu Ala Ala Ala Lys Glu Ala Ala Ala Lys Ala
1               5                   10
```

<210> SEQ ID NO 9
<211> LENGTH: 5
<212> TYPE: PRT
<213> ORGANISM: artificial sequence
<220> FEATURE:
<223> OTHER INFORMATION: Flexible synthetic peptide linker (single
      repeat)

<400> SEQUENCE: 9

Gly Gly Gly Gly Ser
1               5

<210> SEQ ID NO 10
<211> LENGTH: 1424
<212> TYPE: DNA
<213> ORGANISM: Artificial sequence
<220> FEATURE:
<223> OTHER INFORMATION: Synthetic construct, based on murine IL-35;
      details provided in specification

<400> SEQUENCE: 10
cccgggaccg gttacaagga ggttgacaat atgaaaaaga aaattatctc agctattctg        60
atgtctacag tgatactttc tgctgcagcc ccgttgtcag gtgtttacgc tgatactaac       120
gctagcggag ctttagtcgc cttgtctcaa ccacgtgttc aatgtcatgc ttcaagatat       180
ccagtagcag ttgattgctc atggactcca ttacaagctc ctaattctac acgtagtact       240
tcatttattg ccacttaccg cttaggtgtt gcaacacaac agcaatctca gccatgtttg       300
caacgttctc ctcaagcttc aagatgtaca attccagatg tacacttgtt ttcaacagtt       360
ccatatatgc taaatgttac tgcagtacat ccaggtggag ctagttcatc tttgttagca       420
tttgtagctg aacgtattat caaaccagat cctccagaag gagttagact tcgaacagct       480
ggtcagcgtt tacaagtatt gtggcatcca cctgcttctt ggccgtttcc agatattttc       540
agtttgaaat atcgtcttag ataccgtcga cgcggagcat ctcattttcg tcaagttggt       600
ccaattgaag ctacaacttt cacattgcgt aatagtaaac cacatgcaaa gtattgtatt       660
caagtatcag ctcaagatct tacagattat ggtaaaccat ctgattggtc attgcctggt       720
caagtagaaa gtgcaccaca taagccaggt gaagctgcag ccaaagaagc agctgccaaa       780
gctcttgaag cagaagccgc agctaaagaa gccgcagcta aacgtgtaat tccagtttct       840
ggtcctgcta gatgtttatc acaatctcgt aatttgctta aaactacaga tgacatggtt       900
aagactgcta gagaaaaatt gaaacactat tcctgtacag ctgaagatat tgatcatgaa       960
gacattactc gtgatcaaac ttctacattg aaaacatgtt taccacttga attgcataag      1020
aatgagagtt gcttagctac tagagaaaca tcttcaacta cacgtggtag ttgtttacct      1080
ccacaaaaaa cttctttgat gatgactctt tgtcttggtt caatttatga agatttgaaa      1140
atgtatcaaa cagagtttca agctatcaat gctgcattgc aaaatcacaa tcatcaacag      1200
atcattcttg ataaaggaat gttagttgct attgatgaat tgatgcaatc tcttaatcat      1260
aatggtgaaa ctttacgtca aaaaccacct gttggagaag cagatcctta tagagttaag      1320
atgaaacttt gtattctctt acatgctttt tcaacacgag ttgtaactat caatagagtt      1380
atgggatatt tgagttctgc ataagtttaa actctagaac cggt                       1424

<210> SEQ ID NO 11
<211> LENGTH: 457
<212> TYPE: PRT
<213> ORGANISM: artificial sequence
<220> FEATURE:

-continued

```
<223> OTHER INFORMATION: Synthetic construct, based on murine IL-35;
      details provided in specification; encoded by SEQ ID NO: 10

<400> SEQUENCE: 11

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ala Ser
                20                  25                  30

Gly Ala Leu Val Ala Leu Ser Gln Pro Arg Val Gln Cys His Ala Ser
            35                  40                  45

Arg Tyr Pro Val Ala Val Asp Cys Ser Trp Thr Pro Leu Gln Ala Pro
        50                  55                  60

Asn Ser Thr Arg Ser Thr Ser Phe Ile Ala Thr Tyr Arg Leu Gly Val
65                  70                  75                  80

Ala Thr Gln Gln Gln Ser Gln Pro Cys Leu Gln Arg Ser Pro Gln Ala
                85                  90                  95

Ser Arg Cys Thr Ile Pro Asp Val His Leu Phe Ser Thr Val Pro Tyr
            100                 105                 110

Met Leu Asn Val Thr Ala Val His Pro Gly Gly Ala Ser Ser Ser Leu
            115                 120                 125

Leu Ala Phe Val Ala Glu Arg Ile Ile Lys Pro Asp Pro Pro Glu Gly
        130                 135                 140

Val Arg Leu Arg Thr Ala Gly Gln Arg Leu Gln Val Leu Trp His Pro
145                 150                 155                 160

Pro Ala Ser Trp Pro Phe Pro Asp Ile Phe Ser Leu Lys Tyr Arg Leu
                165                 170                 175

Arg Tyr Arg Arg Arg Gly Ala Ser His Phe Arg Gln Val Gly Pro Ile
            180                 185                 190

Glu Ala Thr Thr Phe Thr Leu Arg Asn Ser Lys Pro His Ala Lys Tyr
            195                 200                 205

Cys Ile Gln Val Ser Ala Gln Asp Leu Thr Asp Tyr Gly Lys Pro Ser
        210                 215                 220

Asp Trp Ser Leu Pro Gly Gln Val Glu Ser Ala Pro His Lys Pro Gly
225                 230                 235                 240

Glu Ala Ala Ala Lys Glu Ala Ala Ala Lys Ala Leu Glu Ala Glu Ala
                245                 250                 255

Ala Ala Lys Glu Ala Ala Ala Lys Arg Val Ile Pro Val Ser Gly Pro
            260                 265                 270

Ala Arg Cys Leu Ser Gln Ser Arg Asn Leu Leu Lys Thr Thr Asp Asp
            275                 280                 285

Met Val Lys Thr Ala Arg Glu Lys Leu Lys His Tyr Ser Cys Thr Ala
        290                 295                 300

Glu Asp Ile Asp His Glu Asp Ile Thr Arg Asp Gln Thr Ser Thr Leu
305                 310                 315                 320

Lys Thr Cys Leu Pro Leu Glu Leu His Lys Asn Glu Ser Cys Leu Ala
                325                 330                 335

Thr Arg Glu Thr Ser Ser Thr Thr Arg Gly Ser Cys Leu Pro Pro Gln
            340                 345                 350

Lys Thr Ser Leu Met Met Thr Leu Cys Leu Gly Ser Ile Tyr Glu Asp
            355                 360                 365

Leu Lys Met Tyr Gln Thr Glu Phe Gln Ala Ile Asn Ala Ala Leu Gln
        370                 375                 380

Asn His Asn His Gln Gln Ile Ile Leu Asp Lys Gly Met Leu Val Ala
385                 390                 395                 400
```

-continued

```
Ile Asp Glu Leu Met Gln Ser Leu Asn His Asn Gly Glu Thr Leu Arg
                405                     410                 415

Gln Lys Pro Pro Val Gly Glu Ala Asp Pro Tyr Arg Val Lys Met Lys
                420                     425                 430

Leu Cys Ile Leu Leu His Ala Phe Ser Thr Arg Val Val Thr Ile Asn
            435                 440                     445

Arg Val Met Gly Tyr Leu Ser Ser Ala
        450                 455
```